(12) United States Patent
Guo et al.

(10) Patent No.: US 7,112,605 B2
(45) Date of Patent: Sep. 26, 2006

(54) SULFONYL-CONTAINING 3,4-DIARYL-3-PYRROLIN-2-ONES, PREPARATION METHOD, AND MEDICAL USE THEREOF

(75) Inventors: Zongru Guo, Beijing (CN); Guifang Cheng, Beijing (CN); Fengming Chu, Beijing (CN); Ai Ping Bai, Beijing (CN); Wen Hui Hu, Beijing (CN); Fang Shen, Beijing (CN); Guangzhong Yang, Beijing (CN); Boling Xu, Beijing (CN)

(73) Assignees: Research Institute of Materia Medica Chinese Acadamy of Medical Sciences, Beijing (CN); Jiangsu Hengrui Medicine Company Ltd., Jiangsu Province (CN)

( * ) Notice: Subject to any disclaimer, the term of this patent is extended or adjusted under 35 U.S.C. 154(b) by 0 days.

(21) Appl. No.: 10/437,804

(22) Filed: May 14, 2003

(65) Prior Publication Data

US 2004/0029951 A1     Feb. 12, 2004

Related U.S. Application Data

(63) Continuation of application No. 10/215,400, filed on Aug. 8, 2002, now abandoned.

(51) Int. Cl.
*A61K 31/4015*  (2006.01)
*C07D 207/38*  (2006.01)

(52) U.S. Cl. .................. 514/424; 548/543
(58) Field of Classification Search ............ 548/543; 514/424
See application file for complete search history.

(56) References Cited

U.S. PATENT DOCUMENTS 4,443,616 A * 4/1984 Hofer .................... 548/543
5,466,823 A * 11/1995 Talley et al. ............. 548/377.1

FOREIGN PATENT DOCUMENTS

CN       1318541 A    * 10/2001

OTHER PUBLICATIONS

Bai et al., Design, Synthesis and in vitro Evaluation of a New Class of Novel Cyclooxygenase-2 Inhibitors: 3, 4-diaryl-3-pyrrolin-2-ones, Chinese Chemical Letters vol. 12, No. 9, pp. 775-778, 2001.*
*Abstract only provided.*

* cited by examiner

Primary Examiner—Kamal A. Saeed
Assistant Examiner—Rebecca Anderson
(74) Attorney, Agent, or Firm—Andover-IP-Law; David Silverstein

(57) ABSTRACT

The invention relates to sulfonyl-containing 3,4-diaryl-3-pyrrolin-2-ones compounds having formula (I)

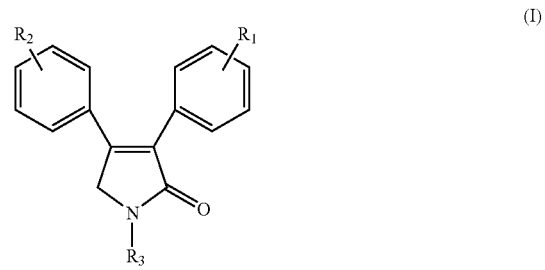

wherein $R_1$ is selected from the group consisting of 4-methylsulfonyl, 4-aminosulfonyl, hydrogen, 2-, 3-, or 4-halogen, $C_1$–$C_6$-alkyl, cyclopentyl, cyclohexyl, $C_1$–$C_4$-alkoxy, hydroxy, cyano, nitro, amino or trifluoromethyl;
$R_2$ is selected from the group consisting of 4-methylsulfonyl, 4-aminosulfonyl, hydrogen, 2-, 3-, or 4-halogen, C1–C6-alkyl, cyclopentyl, cyclohexyl, $C_1$–$C_4$-alkoxy, hydroxy, cyano, nitro, amino or trifluoromethyl; and
$R_3$ is selected from the group consisting of hydrogen, methyl, ethyl, n-propyl, i-propyl, c-propyl, n-butyl, isobutyl; provided that when $R_1$ is a methylsulfonyl or aminosulfonyl group, $R_2$ is any group as defined above except a methylsulfonyl or aminosulfonyl group; and when $R_2$ is a methylsulfonyl or aminosulfonyl group, $R_1$ is any group as defined above except a methylsulfonyl or aminosulfonyl group, also to processes for the preparation of such compounds, to pharmaceutical compositions containing such compounds, and to the medical use of such compounds in the treatment of diseases relating to the inhibition of cyclooxygenase-2 (COX-2).

35 Claims, No Drawings

SULFONYL-CONTAINING 3,4-DIARYL-3-PYRROLIN-2-ONES, PREPARATION METHOD, AND MEDICAL USE THEREOF

This application is a continuation of Ser. No. 10/215,400, filed Aug. 8, 2002, now abandoned.

FIELD OF THE INVENTION

The present invention relates to sulfonyl-containing 3,4-diaryl-3-pyrrolin-2-ones, especially to new compounds of the general formula (I), to a process for their preparation, to pharmaceutical compositions containing such compounds, and to the medical use thereof in the treatment of diseases relating to the inhibition of cyclooxygenase-2 (COX-2), wherein general formula (I) is:

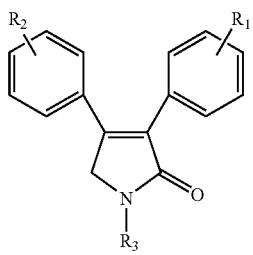

wherein $R_1$ is 4-methylsulfonyl, 4-aminosulfonyl, hydrogen, 2-, 3-, or 4-halogen, including F, Cl or Br, $C_1$–$C_6$-alkyl, cyclopentyl, cyclohexyl, $C_1$–$C_4$-alkoxy, hydroxy, cyano, nitro, amino or trifluoromethyl;

$R_2$ is 4-methylsulfonyl, 4-aminosulfonyl, hydrogen, 2-, 3-, or 4-halogen, C1–C6-alkyl, cyclopentyl, cyclohexyl, $C_1$–$C_4$-alkoxy, hydroxy, cyano, nitro, amino or trifluoromethyl;

$R_3$ is hydrogen, methyl, ethyl, n-propyl, i-propyl, c-propyl, n-butyl, isobutyl. With the proviso that $R_1$ is a methylsulfonyl or aminosulfonyl, $R_2$ is any one group as defined above except a methylsulfonyl or aminosulfonyl group; when $R_1$ is a methylsulfonyl or aminosulfonyl, $R_2$ is any one group as defined above except a methylsulfonyl or aminosulfonyl group.

The halogen of this invention is F, Cl and Br.

TECHNICAL BACKGROUND

Non-steroidal anti-inflammatory drugs (NSAIDs) are used extensively for the treatment of inflammatory conditions, including pain-releasing, anti-pyretic and rheumatoid arthritis. These functions are believed to inhibit the enzyme cyclooxygenase (COX) that is involved in the biosynthesis of prostaglandins G and H from arachidonic acid. So far two isozymes of COX are known: COX-1 and COX-2. COX-1 is constitutively produced in a variety of tissues and appears to be important to the maintenance of normal physiological functions, including gastric and renal cytoprotection. The COX-2 is an inducible isozyme, which is produced in cells under the stimulation of endotoxins, cytokines, and hormones and catalyzes the production of prostaglandins which cause inflammation.

The currently therapeutic use of NSAIDs has been associated with the inhibition of both COX-1 and COX-2 and causes well-known side effects at the gastrointestinal and renal level. Therefore, the selective COX-2 inhibitors could provide anti-inflammatory agents devoid of the undesirable effects associated with classical, nonselective NSAIDs. In addition, COX-2 is over-expressed in colon cancer tissue. COX-2 inhibitors possess potential prophylactic and therapeutic application to colon cancer.

The COX-2 inhibitors as selective anti-inflammatory drugs are chemically aminosulfonylaryl or methylsulfonylaryl-containing substances, such as Nimesulide (R. H. Brogen and A. Ward. Drugs, 1998, 36: 732–753), NS-398 (JP 292856, JP 871119), Meloxicom(DE 2756113, DE 771216), pyrrazole-containing tricyclic compounds, for example, Celecoxib(WO 9641825, WO 961227), oxazole-containing tricyclic compounds, for example, JRE-522(EP 745598, EP 961204), unsaturated gamma-lactone-containing compounds, for example, Rofecoxib (EP 788476, WO 9613483). The non-selective NSAID Indomethacin as a lead compound was chemically modified to give rise to selective COX-2 inhibitors without sulfonyl groups, for example L-748780 and L-761066 (W. C. Black et al. Bioorg Med. Chem. Lett. 1996, 6: 725–742, WO 9730030). These compounds exhibit a selective COX-2 inhibition to different extents, and constitute a group of anti-inflammatory drugs with little adverse reactions. Reports on the sulfonyl-containing 3,4-diphenyl-2,5-dihydropyrrolyl-2-ones and their inhibitory properties for COX-2 has not been found so far in the pharmacological literature.

SUMMARY OF THE INVENTION

In one aspect, the present invention is to provide compounds of sulfonyl-containing 3,4-diaryl-3-pyrrolin-2-ones of general formula (I), as shown below.

In another aspect the present invention is to provide methods of preparing the compounds of sulfonyl-containing 3,4-diaryl-3-pyrrolin-2-ones.

In an additional aspect the present invention provides pharmaceutically acceptable compositions which comprise a therapeutically effective amount of one or more of the compounds of formula (I), as described herein, formulated together with one or more pharmaceutically acceptable carriers.

In a further aspect the present invention provides an application of the compounds of formula (I) to the diseases relevant to COX-2.

In order to complete the purpose of the present invention, the following technique is performed:

This invention encompasses compounds of formula (I)

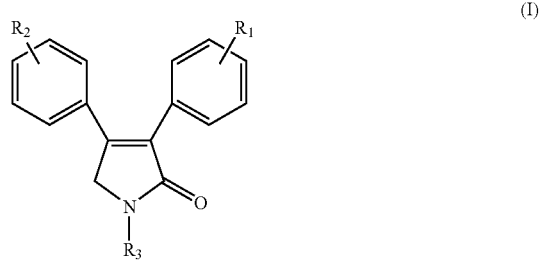

wherein $R_1$ is 4-methylsulfonyl, 4-aminosulfonyl, hydrogen, 2-, 3-, or 4-halogen, including F, Cl or Br, $C_1$–$C_6$-alkyl, cyclopentyl, cyclohexyl, $C_1$–$C_4$-alkoxy, hydroxy, cyano, nitro, amino or trifluoromethyl;

$R_2$ is 4-methylsulfonyl, 4-aminosulfonyl, hydrogen, 2-, 3-, or 4-halogen, C1–C6-alkyl, cyclopentyl, cyclohexyl, $C_1$–$C_4$-alkoxy, hydroxy, cyano, nitro, amino or trifluoromethyl;

$R_3$ is hydrogen, methyl, ethyl, n-propyl, i-propyl, c-propyl, n-butyl, isobutyl. With the proviso that $R_1$ is a methylsulfonyl or aminosulfonyl, $R_2$ is any one group as defined above except a methylsulfonyl or aminosulfonyl group; when $R_1$ is a methylsulfonyl or aminosulfonyl, $R_2$ is any one group as defined above except a methylsulfonyl or aminosulfonyl group.

The halogen of this invention is F, Cl and Br.

Specifically, the present invention comprises the compounds of formula (I), wherein the alkyl of $R_1$ is a methyl or ethyl group, and the alkoxy of $R_1$ is a methoxy group; the alkyl of $R_2$ is a methyl or ethyl group, and the alkoxy of $R_2$ is a methoxy group; and $R_3$ is selected from hydrogen, methyl, ethyl, n-propyl, i-propyl or cyclo-propyl.

A synthetic method was disclosed in the literature (P. Babu and T. R. Balasubramanian, J Indian Chem. 1987, 26B: 63) for preparing 3,4-diaryl-3-pyrrolin-2-ones. The method involves condensation of a substituted alpha-bromoacetophenone with a phenacetamide to form phenacetamido-acetophenone, which is cyclized in triethlamine and acetonitrile on heating to give a diphenyl=dihydropyrrolones. However, this method accompanies production of by-products and restricts synthesis of the compounds with various substituents.

To prepare the compounds of formula (I) defined in this invention, the synthetic method comprises a substitution reaction of a substituted styrene oxide with ammonia or a primary amine at different temperature and various solvents. The resulting amino alcohol, under a controlled condition, reacts with a substituted phenacetyl chloride. Instead of esters, the predominating products of this reaction are amides owing to stronger nucleophibility of amino than that of hydroxy group. The secondary hydroxy group of hydroxy-amines is oxidized using Jone's reagent to give keto-amides, which under an alkali catalysis are cyclized to yield the compounds of the present invention.

Specifically, the method for preparing compounds of formula (I), where $R_1$ stands for 2-, 3-, or 4-substituted groups except methylsulfonyl or aminosulfonyl moieties, $R_2$ represents 4-methylsulfonyl or 4-aminosulfonyl groups, and $R_3$ is the same as the above-mentioned components, comprises the following steps of:

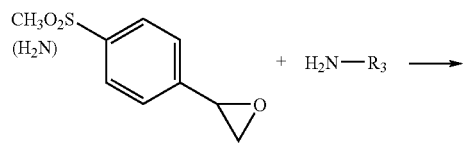

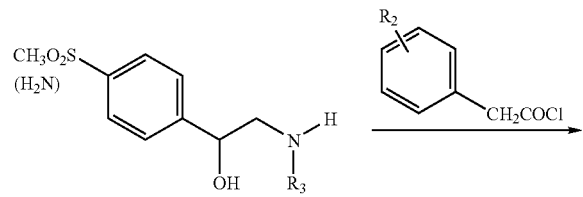

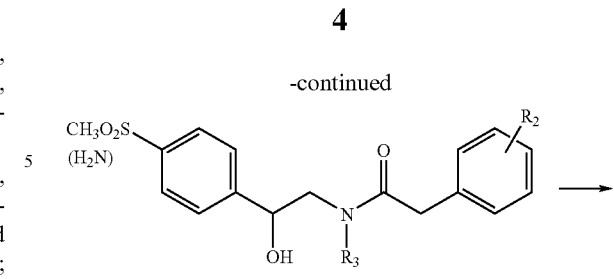

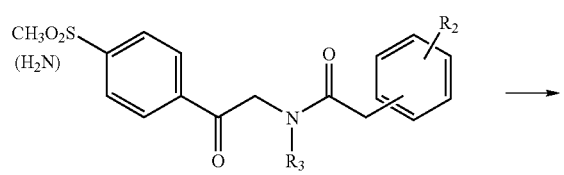

For the compounds of formula (I) where $R_1$ stands for 4-methylsulfonyl or 4-aminosulfonyl groups $R_2$ represents 2-, 3-, or 4-substituted groups except methylsulfonyl or aminosulfonyl moieties, and $R_3$ is the same as the above-mentioned substituents, comprises the following steps of:

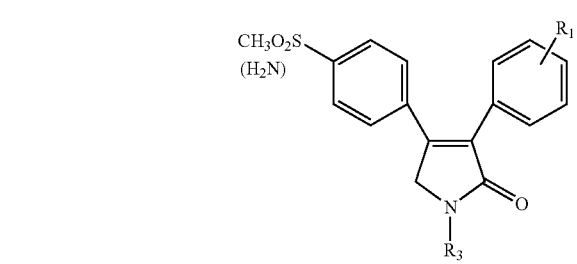

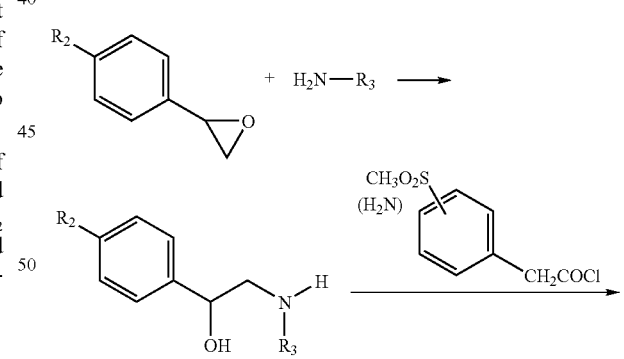

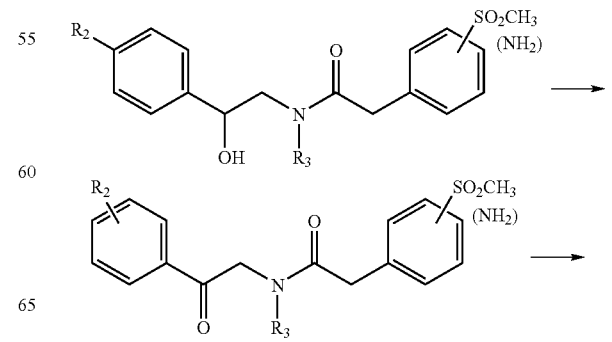

-continued

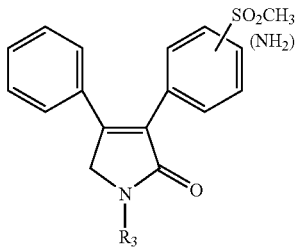

The synthetic feature of above-mentioned schemes is described as follows:

(A) An aminosulfonyl or methylsulfonyl-substituted styrene oxide reacts with a primary amine in a lower alkyl alcohol medium at the temperature from 0□ to 60□, to give rise to N-alkyl-beta-hydroxy-aminosulfonyl(or methylsulfonyl)phenethyl amine;

(B) the resulting N-alkyl-beta-hydroxy-aminosulfonyl(or methylsulfonyl)phenethyl amine is acylated by a phenactyl chloride with optional substituent(s), selected from hydrogen, 2-, 3-, or 4-halogen, $C_1$–$C_6$-alkyl, cyclopentyl, cyclohexyl, $C_1$–$C_4$-alkoxy, hydroxy, cyano, nitro, amino or trifluoromethyl, at room temperature, yielding N-alkyl-N-[2-hydroxy-2-(aminosulfonyl(or methylsulfonyl)phenyl)ethyl-4-substituted pheacetamides;

(C) using Jone's reagent or pyridine-chromic anhydride solution the N-alkyl-N-[2-hydroxy-2-(aminosulfonyl(or methylsulfonyl)phenyl)ethyl-4-substituted pheacetamides are oxidized to give N-alkyl-N-[2-oxo-2-(aminosulfonyl(or methylsulfonyl)phenyl)ethyl-4-substituted pheacetamides;

(D) under the catalysis of potassium or sodium lower alkyl alcoholate the N-alkyl-N-[2-oxo-2-(aminosulfonyl(or methylsulfonyl)phenyl)ethyl-4-substituted pheacetamides cyclize to the title compounds of the present invention.

The present invention provides pharmaceutically acceptable compositions comprising a therapeutically effective amount of one or more of the compounds defined in formula (I).

Pharmacological study reveals that the compounds of formula (I) of the present invention possess inhibitory activity against cyclooxygenase-2, which is produced by the mediation of inflammatory substances; the compounds of formula (I) significantly block mice ear edema induced by carrageenan. More importantly, the inhibitory concentration of compounds of formula (I) against COX-2 does not show any inhibition of COX-1, but shows that the compounds are selectively used for the inhibition of COX-2 or for treatment of COX-2 mediated diseases, especially in the long-term clinical application the compounds of formula (I) would exhibit less adverse reactions, such as less side effects for gastrointestinal and renal organs.

The compounds of formula (I) are useful for relief of pain, fever, inflammation of a variety of conditions including rheumatic fever, symptoms associated with common cold, headache. In addition COX-2 enzyme is highly-expressed in colon and rectum carcinoma, and compounds of formula (I) may inhibit cellular neoplastic transformations and hence can be used in the treatment of colon and rectum cancer.

The typical compounds of the present invention preferably include, but are not limited to:

N-methyl-3-(4-methylsulfonylphenyl)-4-(4-phenyl)-2,5-dihydropyrrole-2-one;
N-methyl-3-(4-methylsulfonylphenyl)-4-(4-chlorophenyl)-2,5-dihydropyrrole-2-one;
N-methyl-3-(4-methylsulfonylphenyl)-4-(4-fluorophenyl)-2,5-dihydropyrrole-2-one;
N-propyl-3-(4-methylsulfonylphenyl)-4-(4-chlorophenyl)-2,5-dihydropyrrole-2-one;
N-methyl-3-(4-aminosulfonylphenyl)-4-(4-phenyl)-2,5-dihydropyrrole-2-one;
N-propyl-3-(4-aminosulfonylphenyl)-4-(4-chlorophenyl)-2,5-dihydropyrrole-2-one;
N-propyl-3-(4-methylsulfonylphenyl)-4-(4-methylphenyl)-2,5-dihydropyrrole-2-one;
N-methyl-3-(4-methylsulfonylphenyl)-4-(4-methylphenyl)-2,5-dihydropyrrole-2-one;
N-propyl-3-(4-methylsulfonylphenyl)-4-(4-fluorophenyl)-2,5-dihydropyrrole-2-one;
N-cycopropyl-3-(4-methylsulfonylphenyl)-4-(4-chlorophenyl)-2,5-dihydropyrrole-2-one;
N-methyl-3-(4-methylsulfonylphenyl)-4-(3-chlorophenyl)-2,5-dihydropyrrole-2-one;
N-propyl-3-(4-methylsulfonylphenyl)-4-(3-chlorophenyl)-2,5-dihydropyrrole-2-one;
N-methyl-3-(4-methylsulfonylphenyl)-4-(4-bromophenyl)-2,5-dihydropyrrole-2-one;
N-methyl-3-pheny-4-1(4-methylsulfonylphenyl)-2,5-dihydropyrrole-2-one;
N-cycopropyl-3-pheny-4-1(4-methylsulfonylphenyl)-2,5-dihydropyrrole-2-one;
N-methyl-3-(4-chlorophenyl)-4-(4-methylsulfonylphenyl)-2,5-dihydropyrrole-2-one;
N-methyl-3-(3-chlorophenyl)-4-(4-methylsulfonylphenyl)-2,5-dihydropyrrole-2-one;
N-methyl-3-(4-bromophenyl)-4-(4-methylsulfonylphenyl)-2,5-dihydropyrrole-2-one;
N-methyl-3-(4-fluorophenyl)-4-(4-methylsulfonylphenyl)-2,5-dihydropyrrole-2-one;
N-propyl-3-(4-aminosulfonylphenyl)-phenyl-4-(3-chlorophenyl)-2,5-dihydropyrrole-2-one;
N-propyl-3-(4-aminosulfonylphenyl)-phenyl-4-(3-bromophenyl)-2,5-dihydropyrrole-2-one; and
N-cycopropyl-3-(4-aminosulfonylphenyl)-phenyl-4-(3-chlorophenyl)-2,5-dihydropyrrole-2-one.

According to the present invention, a pharmaceutical composition containing effective amounts of the compounds of claim 1 and pharmaceutically acceptable carriers is provided.

The present invention is also related to a method for treating inflammatory disease of mammalian animals including humans, by administration of effective amounts of the compounds of formula (I) to a subject.

Preferably, the compounds of the present invention can be administered to a patient in such oral dosage forms as tablets, capsules, pills, or lozenges. Likewise, administration may be effected through parenteral route, such as injection or suppository. All these dosage forms are known to those of ordinary skill in the art or can be determined by routine experimentation. To manufacture tablets, capsules or lozenges, non-toxic pharmaceutically acceptable excipients may be, for example, inert diluents, such as starch, gelatin, acacia, silica, and PEG. Solvents for liquid dosage forms comprise water, ethanol, propylene glycol, vegetable oils such as corn oil, peanut oil and olive oil. Auxiliary components in the dosage forms of the present invention comprise surface active agents, lubricates, disintegrators, sweeteners, disinfectants, and coloring agents.

The amount of active ingredient that may be combined with the carrier and auxiliary materials in a single dosage form will vary depending on the host treated and the particular mode of administration. For example, a formulation intended for the oral administration of patients may contain from about 10 mg to 500 mg of a compound of formula (I). An optimal dosage form typically contains 20 mg to 100 mg of a compound of formula (I).

The following non-limiting examples further describe and illustrate details for the preparation of the compounds of the present invention. The examples are illustrative and do not restrict the scope of the present invention. Those skilled in the art will readily understand and appreciate that known variations of the conditions and procedures in the following preparative methods can be utilized. In these examples, all temperatures are indicated by degrees Celsius, and melting points are uncorrected. Some of the following examples further include nuclear magnetic resonance (H-NMR) data for the subject compounds.

DETAILED DESCRIPTION OF THE INVENTION

Preparation of N-alkyl-β-hydroxy-substituted phenethylamines

EXAMPLE 1

N-Methyl-β-hydroxy-4-methyl-phenethylamine

4-Methyl styrene oxide(1.0 g, 8.0 mmol) and 3 ml of methylamine in methanolic solution(28%) were charged into a flask. The flask was sealed and put in a refrigerator for 5–7 days. The solution was concentrated and the residue crystallized from ether, the title compound was obtained as white needle crystals, mp. 90.5–93.2° C., yield 71.2%.

EXAMPLE 2

N-Methyl-β-3-hydroxy-phenethylamine

The procedure was in the same manner as described in example 1, except that the starting material is styrene oxide (0.96 g) instead of 4-methyl styrene oxide. The title compound was obtained as white needle crystals, mp. 75.0–76.0° C., yield 58.2%.

EXAMPLE 3

N-Methyl-β-hydroxy-4-fluoro-phenethylamine

The procedure was in the same manner as described in example 1, except that the starting material is 4-fluoro-styrene oxide (1.11 g) instead of 4-methyl styrene oxide. The title compound was obtained as white needle crystals, mp. 77.0–78.8° C., yield 87.7%.

EXAMPLE 4

N-Methyl-β-hydroxy-4-chloro-phenethylamine

The procedure was in the same manner as described in example 1, except that the starting material was 4-chloro-styrene oxide(1.24 g) instead of 4-methyl styrene oxide. The title compound was obtained as white needle crystals, mp.84–86° C., yield 31.6%.

EXAMPLE 5

N-Methyl-β-hydroxy-4-bromo-phenethylamine

The procedure was in the same manner as described in example 1, except that the starting material was 4-bromo-styrene oxide (1.59 g) instead of 4-methyl styrene oxide. The title compound was obtained as white needle crystals, mp.91.5–93.7° C., yield 85.7%.

EXAMPLE 6

N-Methyl-β-hydroxy-3-fluoro-phenethylamine

The procedure was in the same manner as described in example 1, except that the starting material is 3-fluoro-styrene oxide (1.11 g) instead of 4-methyl styrene oxide. The title compound was obtained as white needle crystals, mp.63–65° C., yield 32.1%.

EXAMPLE 7

N-Methyl-β-hydroxy-3-chloro-phenethylamine

The procedure was in the same manner as described in example 1, except that the starting material was 3-chloro-styrene oxide(1.24 g) instead of 4-methyl styrene oxide. The title compound was obtained as white needle crystals, mp.95.5–97° C., yield 55.8%.

EXAMPLE 8

N-Methyl-β-hydroxy-3-bromo-phenethylamine

The procedure was in the same manner as described in example 1, except that the starting material was 3-bromo-styrene oxide (1.59 g) instead of 4-methyl styrene oxide. The title compound was obtained as white needle crystals, mp.112.–113.5° C., yield 67.0%.

EXAMPLE 9

N-Propyl-β-hydroxy-4-methyl-phenethylamine

4-Methyl styrene oxide(1.0 g,8.0 mmol)and 3 ml of propylamine in methanolic solution were charged into a flask. The flask was sealed and put in a refrigerator for 5–7 days. The solution was concentrated and the residue crystallized from ether, the title compound was obtained as white needle crystals, mp. 73.0–75.1 C, yield 49.6%.

EXAMPLE 10

N-Propyl-β-hydroxy-4-fluoro-phenethylamine

The procedure was in the same manner as described in example 9, except that the starting material was 4-fluoro-styrene oxide (1.11 g) instead of 4-Methyl styrene oxide. The title compound was obtained as white needle crystals, mp. 58.6–78.8° C., yield 74.1%.

EXAMPLE 11

N-Propyl-β-hydroxy-3-chloro-phenethylamine

The procedure was in the same manner as described in example 9, except that the starting material was 3-chlorostyrene oxide (1.24 g) instead of 4-Methyl styrene oxide. The title compound was obtained as white needle crystals, mp. 79.5–80.5° C., yield 31.6%.

EXAMPLE 12

N-Propyl-β-hydroxy-4-bromo-phenethylamine

The procedure was in the same manner as described in example 9, except that the starting material was 4-bromo-styrene oxide (1.59 g) instead of 4-Methyl styrene oxide. The title compound was obtained as white needle crystals, mp. 72.5–74.5° C., yield 64.6%.

EXAMPLE 13

N-Propyl-β-hydroxy-3-fluoro-phenethylamine

The procedure was in the same manner as described in example 9, except that the starting material was 3-fluoro-styrene oxide (1.11 g) instead of 4-Methyl styrene oxide. The title compound was obtained as white needle crystals, mp. 46–47.3° C., yield 31.9%.

EXAMPLE 14

N-Propyl-β-hydroxy-3-chloro-phenethylamine

The procedure was in the same manner as described in example 9, except that the starting material was 3-chloro-styrene oxide (1.24 g) instead of 4-Methyl styrene oxide. The title compound was obtained as white needle crystals, mp. 69.5–71.0° C., yield 50.9%.

EXAMPLE 15

N-Propyl-β-hydroxy-3-bromo-phenethylamine

The procedure was in the same manner as described in example 9, except that the starting material was 3-bromo-styrene oxide (1.59 g) instead of 4-Methyl styrene oxide. The title compound was obtained as white needle crystals, mp. 79.7–81.4° C., yield 80.5%.

EXAMPLE 16

N-Cyclopropyl-β-hydroxy-4-chloro-phenethylamine

4-Chloro styrene oxide (1.24 g, 8.0 mmol) and 3 ml of cyclopropylamine in methanolic solution were charged into a flask. The flask was sealed and put in a refrigerator for 5–7 days. The solution was concentrated and the residue crystallized from ether, the title compound was obtained as white needle crystals, mp. 100.2–102° C., yield 54.5%.

EXAMPLE 17

N-Cyclopropyl-β-hydroxy-4-bromo-phenethylamine

The procedure was in the same manner as described in example 16, except that the starting material was 4-bromo-styrene oxide (1.59 g) instead of 4-chloro styrene oxide. The title compound was obtained as white needle crystals, mp. 105.4–107.4° C., yield 79.4%.

EXAMPLE 18

N-Cyclopropyl-β-hydroxy-3-fluoro-phenethylamine

The procedure was in the same manner as described in example 16, except that the starting material was 4-fluoro-styrene oxide(1.11 g) instead of 4-chloro styrene oxide. The title compound was obtained as white needle crystals, mp. 57.8–60.0° C., yield 31.6%.

EXAMPLE 19

N-Cyclopropyl-β-hydroxy-3-chloro-phenethylamine

The procedure was in the same manner as described in example 16, except that the starting material was 3-chloro-styrene oxide(1.24 g) instead of 4-chloro styrene oxide. The title compound was obtained as white needle crystals, mp. 71.3–73.2° C., yield 62.0%.

EXAMPLE 20

N-Cyclopropyl-β-hydroxy-3-bromo-phenethylamine

The procedure was in the same manner as described in example 16, except that the starting material was 3-bromo-styrene oxide(1.59 g) instead of 4-chloro styrene oxide. The title compound was obtained as white needle crystals, mp. 69.5–70.4° C., yield 62.7%.

EXAMPLE 21

N-Methyl-β-hydroxy-4-methylsulfonyl-phenethylamine

The procedure was in the same manner as described in example 1, except that the starting material was 4-methylsulfonyl-styrene oxide (1.58 g) instead of 4-methyl styrene oxide. The title compound was obtained as white crystals, mp. 110–112 C, yield 57.0%.

EXAMPLE 22

N-Propyl-β-hydroxy-4-methylsulfonyl-phenethylamine

The procedure was in the same manner as described in example 9, except that the starting material was 4-methylsulfonyl-styrene oxide (1.58 g) instead of 4-methyl styrene oxide. The title compound was obtained as white solid, mp.120–123° C., yield 85.0%.

EXAMPLE 23

N-Cyclopropyl-β-hydroxy-4-methylsulfonyl-phenethylamine

The procedure was in the same manner as described in example 16, except that the starting material was 4-methylsulfonyl-styrene oxide(1.58 g) instead of 4-chloro styrene oxide. The title compound was obtained as white solid, yield 70.0%.

Preparation of Methylsulfonyl (or Aminosulfonyl)Phenacetyl Chlorides

EXAMPLE 24

4-Methylsulfonyl (or Aminosulfonyl)Phenacetyl Chloride

A mixture of 1.5 mmol of 4-methylsulfonyl (or aminosulfonyl)phenacetic acid and 5 ml of thionyl chloride was heated under reflux and in nitrogen atmosphere to give a clear solution. Removal of the excess of thionyl chloride under reduced pressure a light yellow solid was obtained and without purification put into the next reaction.

Preparation of N-alkyl-N-2-hydroxy-2-substituted phenyl ethyl-4-methyl(amino) sulfonyl)phenacetamides

EXAMPLE 25

N-Methyl-N-(2-hydroxy-phenylethyl-4-methylsulfonylphenacetamide

To a solution of 1.5 mmol of N-methyl-β-hydroxy-phenethylamine described in Example 2 in 20 ml of re-distilled THF was added with stirring 4.5 mmol of triethylamine in nitrogen atmosphere. To the mixture was rapidly added a solution of 1.5 mmol of 4-methylsulfonyl phenacetyl chloride (Example 24)in 10 ml of redistilled THF. The resulting white precipitate was filtered off. The filtrate was evaporated and the residue was purified by column chromatograph on silica gel (eluent:ethyl acetate:methyle chloride—1:2–3) to give white solid, mp. 160–161° C., yield: 90.0%.

EXAMPLE 26

N-Propyl-N-[2-hydroxy-2-(4-methylphenyl)]ethyl-4-methylsulfonylphenacetamide

The procedure was in the same manner as described in Example 25, except that the starting material was N-propyl-β-hydroxy-4-methylphenethylamine instead of N-methyl-β-hydroxy-phenethylamine. The title compound was obtained yield 46.5%.

EXAMPLE 27

N-Methyl-N-[2-hydroxy-2-(4-methylphenyl]ethyl-4-methylsulfonylphenacetamide

The procedure was in the same manner as described in Example 25, except that the starting material was N-methyl-β-hydroxy-4-methylphenethylamine instead of N-methyl-β-hydroxy-phenethylamine. The title compound was obtained as white solid, yield 44.0%.

EXAMPLE 28

N-Propyl-N-[2-hydroxy-2-(4-fluorophenyl)]ethyl-4-methylsulfonylphenacetamide

The procedure was in the same manner as described in example 25, except that the starting material was N-propyl-β-hydroxy-4-fluorophenethylamine instead of N-methyl-β-hydroxy-phenethylamine. The title compound was obtained as white solid, 51.4%.

EXAMPLE 29

N-Cyclopropyl-N-[2-hydroxy-2-(4-chlorophenyl]ethyl-4-methylsulfonylphenacetamide The procedure was in the same manner as described in example 25, except that the starting material was N-cyclopropyl-β-hydroxy-4-chlorophenethylamine instead of N-methyl-β-hydroxy-phenethylamine. The title compound was obtained as white solid, 51.4%.

EXAMPLE 30

N-Cyclopropyl-N-[2-hydroxy-2-(3-chlorophenyl)]ethyl-4-methylsulfonylphenacetamide The procedure was in the same manner as described in example 25, except that the starting material was N-cyclopropyl-β-hydroxy-3-chlorophenethylamine instead of N-methyl-β-hydroxy-phenethylamine. The obtained title compound was used directly into the oxidation reaction of the next reaction.

EXAMPLE 31

N-Methyl-N-[2-hydroxy-2-(3-chlorophenyl)]ethyl-4-methylsulfonylphenacetamide

The procedure was in the same manner as described in example 25, except that the starting material was N-methyl-β-hydroxy-3-chlorophenethylamine prepared in Example 4 instead of N-methyl-β-hydroxy-phenethylamine. The title compound was obtained as white solid, mp. 207–208° C., yield 89.5%.

EXAMPLE 32

N-Propyl-N-[2-hydroxy-2-(3-chlorophenyl)]ethyl-4-methylsulfonylphenacetamide

The procedure was in the same manner as described in example 25, except that the starting material was N-n-propyl-β-hydroxy-3-chlorophenethylamine prepared in Example 11 instead of N-methyl-β-hydroxy-phenethylamine. The title compound was obtained as white solid, mp. 124–125° C., yield 90.0%.

EXAMPLE 33

N-Methyl-N-[2-hydroxy-2-(3-bromophenyl)]ethyl-4-methylsulfonylphenacetamide

The procedure was in the same manner as described in example 25, except that the starting material was N-methyl-β-hydroxy-3-bromophenethylamine instead of N-methyl-β-hydroxy-phenethylamine. The title compound was obtained as light yellow oil, yield 45.4%.

EXAMPLE 34

N-Cyclohexyl-N-(2-hydroxy-2-phenyl)ethyl-4-methylsulfonylphenacetamide

The procedure was in the same manner as described in example 25, except that the starting material was N-cyclohexyl-β-hydroxy-2-phenethylamine instead of N-methyl-β- hydroxy-phenethylamine. The title compound was obtained as light yellow oil, yield 55.6%.

EXAMPLE 35

N-Cyclopropyl-N-[2-hydroxy-2-(3-fluorophenyl)]ethyl-4-methylsulfonylphenacetamide The procedure was in the same manner as described in example 25, except that the starting material is N-cyclopropyl-β-hydroxy-2-(3-flurophenethyl)amine instead of N-methyl-β-hydroxy-phenethylamine. The title compound was obtained as light yellow oil, yield 47.3%.

Preparation of N-alkyl-N-[2-hydroxy-2-(4-methylsulfonylphenyl)]ethyl-substituted phenacetamides

EXAMPLE 36

N-Methyl-N-[2-hydroxy-2-(4-methylsulfonylphenyl)]ethyl-phenacetamide

To a solution of 1.5 mmol of N-methyl-β-hydroxy-4-methylsulfonylphenethylamine described in Example 21 in 20 ml of pyridine was added with stirring phenacetyl chloride in nitrogen atmosphere. The mixture was stirred at room temperature until the reaction was completed. The resulting white precipitate was filtered off. The filtrate was evaporated and the residue was purified by column chromatograph on silica gel (eluent: ethyl acetate:methyl chloride—1:2–3) to give the title compound as a pale yellow oil, yield: 52.6%.

EXAMPLE 37

N-Propyl-N-[2-hydroxy-2-(4-methylsulfonylphenyl)]ethyl-phenacetamide

The procedure was in the same manner as described in example 36, except that the starting material was N-propyl-β-hydroxy-4-methylsulfonylphenethylamine instead of N-methyl-β-hydroxy-4-methylsulfonylphenethylamine. The obtained title compound was pale yellow oil, yield 50.0%.

EXAMPLE 38

N-Cyclopropyl-N-[2-hydroxy-2-(4-methylsulfonylphenyl)]ethyl-phenacetamide

The procedure was in the same manner as described in example 36, except that the starting material was N-cyclopropyl-β-hydroxy-4-methylsulfonylphenethylamine instead of N-methyl-β-hydroxy-4-methylsulfonylphenethylamine. The obtained title compound was pale yellow oil and used directly into the oxidation reaction of the next reaction.

EXAMPLE 39

N-Methyl-N-[2-hydroxy-2-(4-methylsulfonylphenyl)]ethyl-4-chlorophenacetamide

The procedure was in the same manner as described in example 36, except that the starting material was 4-chlorophenacetyl chloride instead of phenacetyl chloride. The obtained title compound was pale yellow oil, yield 60.0%.

EXAMPLE 40

N-Methyl-N-[2-hydroxy-2-(4-methylsulfonylphenyl)]ethyl-3-chlorophenacetamide

The procedure was in the same manner as described in example 36, except that the starting material was 3-chlorophenacetyl chloride instead of phenacetyl chloride. The obtained title compound was pale yellow oil, yield 50.4%.

EXAMPLE 41

N-Methyl-N-[2-hydroxy-2-(4-methylsulfonylphenyl)]ethyl-4-bromophenacetamide

The procedure is in the same manner as described in example 37, except that the starting material was 4-bromophenacetyl chloride instead of phenacetyl chloride. The obtained title compound was pale yellow oil and used directly into the oxidation reaction of the next reaction.

EXAMPLE 42

N-Methyl-N-[2-hydroxy-2-(4-methylsulfonylphenyl)]ethyl-4-fluorophenacetamide

The procedure was in the same manner as described in example 36, except that the starting material was 4-fluorophenacetyl chloride instead of phenacetyl chloride. The obtained title compound was pale yellow oil and used directly into the oxidation reaction of the next reaction.

EXAMPLE 43

N-Propyl-N-[2-hydroxy-2-(4-methylsulfonylphenyl)]ethyl-3-methylphenacetamide

The procedure was in the same manner as described in example 36, except that the starting materials were N-propyl-β-hydroxy-4-methylsulfonylphenethylamine and 3-methylphenacetyl chloride instead of N-methyl-β-hydroxy-4-methylsulfonylphenethylamine and phenacetyl chloride, respectively. The obtained title compound was a pale yellow oil and used directly into the oxidation reaction of the next reaction.

EXAMPLE 44

N-Propyl-N-[2-hydroxy-2-(4-methylsulfonylphenyl)]ethyl-4-methylphenacetamide

The procedure was in the same manner as described in example 36, except that the starting materials were N-propyl-β-hydroxy-4-methylsulfonylphenethylamine and 4-methylphenacetyl chloride instead of N-methyl-β-hydroxy-4-methylsulfonylphenethylamine and phenacetyl chloride, respectively. The obtained title compound was a pale yellow oil and used directly into the oxidation reaction of the next reaction.

EXAMPLE 45

N-Propyl-N-[2-hydroxy-2-(4-methylsulfonylphenyl)]ethyl-4-fluorophenacetamide

The procedure was in the same manner as described in example 36, except that the starting materials were N-propyl-β-hydroxy-4-methylsulfonylphenethylamine and 4-fluorophenacetyl chloride instead of N-methyl-β-hydroxy-4-methylsulfonylphenethylamine and phenacetyl chloride, respectively. The obtained title compound was pale yellow oil and used directly into the oxidation reaction of the next reaction.

EXAMPLE 46

N-Propyl-N-[2-hydroxy-2-(4-methylsulfonylphenyl)]ethyl-4-chlorophenacetamide

The procedure was in the same manner as described in example 36, except that the starting materials were N-propyl-β-hydroxy-4-methylsulfonylphenethylamine and 4-chlorophenacetyl chloride instead of N-methyl-β-hydroxy-4-methylsulfonylphenethylamine and phenacetyl chloride, respectively. The obtained title compound was a pale yellow oil and used directly into the oxidation reaction of the next reaction.

EXAMPLE 47

N-Cylcopropyl-N-[2-hydroxy-2-(4-methylsulfonylphenyl)]ethyl-4-methylphenacetamide The procedure was in the same manner as described in example 36, except that the starting materials are N-cyclopropyl-β-hydroxy-4-methylsulfonylphenethylamine and 4-methylphenacetyl chloride instead of N-methyl-β-hydroxy-4-methylsulfonylphenethylamine and phenacetyl chloride, respectively. The obtained title compound was pale yellow oil and used directly into the oxidation reaction of the next reaction.

EXAMPLE 48

N-Cyclopropyl-N-[2-hydroxy-2-(4-methylsulfonylphenyl)]methyl-3-methylphenacetamide The procedure was in the same manner as described in example 36, except that the starting materials were N-cyclopropyl-β-hydroxy-4-methylsulfonylphenethylamine and 3-methylphenacetyl chloride instead of N-methyl-β-hydroxy-4-methylsulfonylphenethylamine and phenacetyl chloride, respectively. The obtained title compound was a pale yellow oil and used directly into the oxidation reaction of the next reaction.

EXAMPLE 49

N-Cyclohexyl-N-[2-hydroxy-2-(4-methylsulfonylphenyl)]ethyl-4-chlorophenacetamide The procedure was in the same manner as described in example 36, except that the starting materials were N-cyclopropyl-β-hydroxy-4-methylsulfonylphenethylamine and 4-chlorophenacetyl chloride instead of N-methyl-β-hydroxy-4-methylsulfonylphenethylamine and phenacetyl chloride, respectively. The obtained title compound was pale yellow oil and used directly into the oxidation reaction of the next reaction.

EXAMPLE 50

N-Cylcopropyl-N-[2-hydroxy-2-(4-methylsulfonylphenyl]ethyl-4-fluorophenacetamide The procedure was in the same manner as described in example 36, except that the starting materials were N-cyclopropyl-β-hydroxy-4-methylsulfonylphenethylamine and 4-fluorophenacetyl chloride instead of N-methyl-β-hydroxy-4-methylsulfonylphenethylamine and phenacetyl chloride, respectively. The obtained title compound was pale yellow oil and used directly into the oxidation reaction of the next reaction.

EXAMPLE 51

N-Methyl-N-[2-hydroxy-2-(4-methylsulfonylphenyl)]ethyl-3-methylphenacetamide

The procedure was in the same manner as described in example 36, except that the starting material was 3-methylphenacetyl chloride instead of phenacetyl chloride. The obtained title compound was pale yellow oil and used directly into the oxidation reaction of the next reaction.

EXAMPLE 52

N-Methyl-N-[2-hydroxy-2-(4-methylsulfonylphenyl)]ethyl-2,4-dimethylphenacetamide The procedure was in the same manner as described in example 36, except that the starting material was 2,4-dimethylphenacetyl chloride instead of phenacetyl chloride. The obtained title compound was pale yellow oil and used directly into the oxidation reaction of the next reaction.

EXAMPLE 53

N-Propyl-N-[2-hydroxy-2-(4-methylsulfonylphenyl]ethyl-4-phenoxyphenacetamide

The procedure was in the same manner as described in example 36, except that the starting materials were N-propyl-β-hydroxy-4-methylsulfonylphenethylamine and 4-phenoxyacetyl chloride instead of N-methyl-β-hydroxy-4-methylsulfonylphenethylamine and phenacetyl chloride, respectively. The obtained title compound was pale yellow oil and used directly into the oxidation reaction of the next reaction.

EXAMPLE 54

N-Propyl-N-[2-hydroxy-2-(3-bromophenyl)]ethyl-4-aminosulfonylphenacetamide

The procedure was in the same manner as described in example 25, except that the starting materials were aminosulfonyl phenacetyl chloride and N-propyl-β-hydroxy-3-bromophenethylamine instead of 4-methylsulfonyl phenacetyl chloride and N-methyl-β-hydroxyphenethylamine, respectively. The title compound was obtained, yield 22.8%.

EXAMPLE 55

N-Propyl-N-[2-hydroxy-2-(3-chlorophenyl)]ethyl-4-aminosulfonylphenacetamide

The procedure was in the same manner as described in example 25, except that the starting materials were aminosulfonyl phenacetyl chloride and N-propyl-β-hydroxy-3-chlorophenethylamine instead of 4-methylsulfonyl phenacetyl chloride and N-methyl-β-hydroxyphenethylamine, respectively. The title compound was obtained as light yellow oil, yield 45.2%.

EXAMPLE 56

N-Cycopropyl-N-[2-hydroxy-2-(4-chlorophenyl)]ethyl-4-aminosulfonylphenacetamide

The procedure was in the same manner as described in example 25, except that the starting materials were aminosulfonyl phenacetyl chloride and N-propyl-β-hydroxy-4-chlorophenethylamine instead of 4-methylsulfonyl phenacetyl chloride and N-methyl-β-hydroxyphenethylamine, respectively. The title compound was obtained as light yellow oil, yield 28.1%.

EXAMPLE 57

N-Propyl-N-[2-hydroxy-2-(3-fluorophenyl)]ethyl-4-aminosulfonylphenacetamide

The procedure was in the same manner as described in example 25, except that the starting materials were aminosulfonyl phenacetyl chloride and N-propyl-β-hydroxy-3-fluorophenethylamine instead of 4-methylsulfonyl phenacetyl chloride and N-methyl-β-hydroxyphenethylamine, respectively. The title compound was obtained as light yellow oil, yield 32.3%.

EXAMPLE 58

N-Propyl-N-[2-hydroxy-2-(4-fluorophenyl)]ethyl-4-aminosulfonylphenacetamide

The procedure was in the same manner as described in example 25, except that the starting materials were aminosulfonyl phenacetyl chloride-and N-propyl-β-hydroxy-4-fluorophenethylamine instead of 4-methylsulfonyl phenacetyl chloride and N-methyl-β-hydroxyphenethylamine, respectively. The title compound was obtained as light yellow oil, yield 29.4%.

EXAMPLE 59

N-Cycopropyl-N-[2-hydroxy-2-(3-chlorophenyl)]ethyl-4-aminosulfonylphenacetamide

The procedure was in the same manner as described in example 25, except that the starting materials were aminosulfonyl phenacetyl chloride and N-propyl-β-hydroxy-3-chlorophenethylamine instead of 4-methylsulfonyl phenacetyl chloride and N-methyl-β-hydroxyphenethylamine, respectively. The title compound was obtained as light yellow oil, yield 13.8%.

EXAMPLE 60

N-Cycopropyl-N-[2-hydroxy-2-(4-fluorophenyl)]ethyl-4-aminosulfonylphenacetamide

The procedure was in the same manner as described in example 25, except that the starting materials were aminosulfonyl phenacetyl chloride and N-cyclopropyl-β-hydroxy-4-fluorophenethylamine instead of 4-methylsulfonyl phenacetyl chloride and N-methyl-β-hydroxyphenethylamine, respectively. The title compound was obtained as light yellow oil, yield 28.7%.

EXAMPLE 61

N-Propyl-N-[2-hydroxy-2-(3-bromophenyl)]ethyl-4-aminosulfonylphenacetamide

The procedure was in the same manner as described in example 25, except that the starting materials were aminosulfonyl phenacetyl chloride and N-propyl-β-hydroxy-3-bromophenethylamine instead of 4-methylsulfonyl phenacetyl chloride and N-methyl-β-hydroxyphenethylamine, respectively. The title compound was obtained as light yellow oil, yield 28.7%.

EXAMPLE 62

N-Cycopropyl-N-[2-hydroxy-2-(4-methylphenyl)]ethyl-4-aminosulfonylphenacetamide

The procedure was in the same manner as described in example 25, except that the starting materials were aminosulfonyl phenacetyl chloride and N-cyclopropyl-β-hydroxy-4-methylphenethylamine instead of 4-methylsulfonyl phenacetyl chloride and N-methyl-β-hydroxyphenethylamine, respectively. The title compound was obtained as light yellow oil, yield 29.6%.

EXAMPLE 63

N-Cycopropyl-N-[2-hydroxy-2-(3-methylphenyl)]ethyl-4-aminosulfonylphenacetamide

The procedure is in the same manner as described in example 25, the starting materials are aminosulfonyl phenacetyl chloride and N-cyclopropyl-β-hydroxy-4-methylphenethylamine instead of 4-methylsulfonyl phenacetyl chloride and N-methyl-β-hydroxyphenethylamine, respectively. The title compound was obtained as light yellow oil, yield 37.6%.

Preparation of N-alkyl-N-[2-oxo-2-substituted phenyl]ethyl-4-methylsulfonyl(or aminosulfonyl)phenacetamides

EXAMPLE 64

N-Methyl-N-(2-oxo-phenyl)ethyl-4-methylsulfonylphenacetamide

To a hot solution of N-methyl-N-(2-hydroxy-2-phenyl)ethyl-4-methylsulfonyl phenacetamide (prepared in accordance with Example 25) in 25 ml of acetone was added with stirring 3 ml of Jone's reagent. The mixture was stirred until the starting material disappeared, as monitored by TLC. To the reaction mixture was added 10 ml of isopropanol and the solution turned green in color. This solution was evaporated and the residue was mixed with ethyl acetate/water (50 ml/50 ml). The aqueous phase was extracted with 3×20 ml of ethyl acetate. The combined organic phase was washed with water until it reached a pH 7 and then was dried over sodium sulfate. The solvent was evaporated and the residue was purified by column chromatograph on silica gel (eluent: ethyl acetate:methyle chloride—1:1–2) to give the title compound as a white solid. Mp. 132–133° C., yield: 79.5%.

EXAMPLE 65

N-Propyl-N-[2-oxo-2-(4-methylphenyl)]ethyl-4-methylsulfonylphenacetamide

The procedure was in the same manner as described in example 64, except that the starting material was N-cyclopropyl-N-[2-hydroxy-2-(4-methylphenyl)]-ethyl-4-methylsulfonyl phenacetamide instead of N-methyl-N-(2-hydroxy-2-phenyl) ethyl-4-methylsulfonyl phenacetamide. The title compound was obtained as a yellow oil, yield 59.0%.

EXAMPLE 66

N-Methyl-N-[2-oxo-2-(4-methylphenyl)]ethyl-4-methylsulfonylphenacetamide

The procedure was in the same manner as described in example 64, except that the starting material was N-methyl-N-[2-hydroxy-2-(4-methylphenyl)]ethyl-4-methylsulfonyl phenacetamide instead of N-methyl-N-(2-hydroxy-2-phenyl) ethyl-4-methylsulfonyl phenacetamide. The title compound was obtained as yellow oil, yield 49.0%.

EXAMPLE 67

N-Propyl-N-[2-oxo-2-(4-fluorophenyl)]ethyl-4-methylsulfonylphenacetamide

The procedure was in the same manner as described in example 64, except that the starting material was N-cyclopropyl-N-[2-hydroxy-2-(4-fluorophenyl)]ethyl-4-methylsulfonyl phenacetamide instead of N-methyl-N-(2-hydroxy-2-phenyl) ethyl-4-methylsulfonyl phenacetamide. The title compound was obtained as yellow oil, yield 50.0%.

EXAMPLE 68

N-Cyclopropyl-N-[2-oxo-2-(4-chlorophenyl)]ethyl-4-methylsulfonylphenacetamide

The procedure was in the same manner as described in example 64, except that the starting material was N-cyclopropyl-N-[2-hydroxy-2-(4-chlorophenyl)]ethyl-4-methylsulfonyl phenacetamide instead of N-methyl-N-(2-hydroxy-2-phenyl) ethyl-4-methylsulfonyl phenacetamide. The title compound was obtained as yellow oil, yield 50.0%.

EXAMPLE 69

N-Cyclopropyl-N-[2-oxo-2-(3-chlorophenyl)]ethyl-4-methylsulfonylphenacetamide

The procedure was in the same manner as described in example 64, except that the starting material was N-cyclopropyl-N-[2-hydroxy-2-(3-chlorophenyl)]ethyl-4-methylsulfonyl phenacetamide instead of N-methyl-N-(2-hydroxy-2-phenyl) ethyl-4-methylsulfonyl phenacetamide. The title compound was obtained as yellow oil, yield 46.9%.

EXAMPLE 70

N-Methyl-N-[2-oxo-2-(3-chlorophenyl)]ethyl-4-methylsulfonylphenacetamide

The procedure was in the same manner as described in example 64, except that the starting material is N-methyl-N-[2-hydroxy-2-(3-chlorophenyl)]ethyl-4-methylsulfonyl phenacetamide instead of N-methyl-N-(2-hydroxy-2-phenyl) ethyl-4-methylsulfonyl phenacetamide. The title compound was obtained as yellow oil, yield 70.6%.

EXAMPLE 71

N-Propyl-N-[2-oxo-2-(3-chlorophenyl)]ethyl-4-methylsulfonylphenacetamide

The procedure was in the same manner as described in example 64, except that the starting material was N-propyl-N-[2-hydroxy-2-(3-chlorophenyl)]ethyl-4-methylsulfonyl phenacetamide instead of N-methyl-N-(2-hydroxy-2-phenyl) ethyl-4-methylsulfonyl phenacetamide. The title compound was obtained as yellow oil, yield 46.8%.

EXAMPLE 72

N-Methyl-N-[2-oxo-2-(3-bromophenyl)]ethyl-4-methylsulfonylphenacetamide

The procedure was in the same manner as described in example 64, except that the starting material was N-methyl-N-[2-hydroxy-2-(3-bromophenyl)]ethyl-4-methylsulfonyl phenacetamide instead of N-methyl-N-(2-hydroxy-2-phenyl) ethyl-4-methylsulfonyl phenacetamide. The title compound was obtained as yellow oil, yield 46.8%.

EXAMPLE 73

N-Cyclohexyl-N-(2-oxo-2-phenylethyl-4-methylsulfonylphenacetamide

The procedure was in the same manner as described in example 64, except that the starting material was N-cyclohexyl-N-[2-hydroxy-2-phenyl]ethyl-4-methylsulfonyl phenacetamide instead of N-methyl-N-(2-hydroxy-2-phenyl) ethyl-4-methylsulfonyl phenacetamide. The title compound was obtained as a yellow oil, yield 49.5%.

EXAMPLE 74

N-Cyclopropyl-N-[2-oxo-2-(3-fluorophenyl)]ethyl-4-methylsulfonylphenacetamide

The procedure was in the same manner as described in example 64, except that the starting material was N-cyclopropyl-N-[2-hydroxy-2-(3-fluorophenyl)]ethyl-4-methylsulfonyl phenacetamide instead of N-methyl-N-(2-hydroxy-2-phenyl) ethyl-4-methylsulfonyl phenacetamide. The title compound was obtained as yellow oil, yield 51.7%.

Preparation of N-alkyl-N-[2-oxo-2-(4-methylsulfonyl or 4-aminosulfonyl)phenyl]ethyl-substituted phenacetamides

EXAMPLE 75

N-Methyl-N-[2-oxo-2-(4-methylsulfonylphenyl)]ethyl-phenacetamide

To a hot solution of N-methyl-N-[2-hydroxy-2-(4-methylsulfonylphenyl)]ethyl-phenacetamide (prepared in accordance with Example 43) in 25 ml of acetone was added with stirring 3 ml of Jone's reagent. The mixture was stirred until the starting material disappeared, as monitored by TLC. To the reaction mixture was added 10 ml of isopropanol and the solution turned green in color. This solution was then evaporated and the residue was mixed with ethyl acetate/water(50 ml/50 ml). The aqueous phase was extracted with 3×20 ml of ethyl acetate. The combined organic phase was washed with water until it reached a pH 7 and then dried over sodium sulfate. The solvent was evaporated and the residue was purified by column chromatograph on silica gel (eluent: ethyl acetate:methyle chloride—1:1–2) to give the title compound as a pale yellow solid. Mp. 97.6–99° C., yield: 41.0%. $M^+$=345

EXAMPLE 76

N-Propyl-N-[2-oxo-2-(4-methylsulfonylphenyl)]ethyl-phenacetamide

The procedure was in the same manner as described in Example 75, except that the starting material was N-propyll-N-[2-hydroxy-2-(4-methylsulfonylphenyl)]ethyl-phenacetamide instead of N-methyl-N-(2-hydroxy-2-phenyl) ethyl-4-methylsulfonyl phenacetamide. The title compound was obtained as a pale yellow solid, mp. 156–157° C. yield 48.7%.

$M^+$=373, $C_{20}H_{23}NO_4S$ $^1$H-NMR: δ8.14–7.25 (dd, 4H, ArH, J=8.4), 7.36–7.25 (m, 4H, ArH), 4.74 (s, 2H, $CH_2$), 3.83 (s, 3H, CH3), 3.40–3.34 (t, 2H, CH2, J=7.2), 3.07 (s, 3H, $SO_2CH_3$), 1.58–1.50 (m, 2H, $NCH_2$), 0.91–0.86 (t, 3H, $CH_3$, J=7.2)

EXAMPLE 77

N-Cyclopropyl-N-[2-oxo-2-(4-methylsulfonylphenyl)]ethyl-phenacetamide

The procedure was in the same manner as described in Example 75, except that the starting material was N-cyclopropyl-N-[2-hydroxy-2-(4-methylsulfonylphenyl)]ethyl-phenacetamide instead of N-methyl-N-[2-hydroxy-2-(4-methylsulfonylphenyl)]ethyl-phenacetamide. The title compound was obtained as a yellow oily liquid, yield: 41.7%. $M^+$=405

EXAMPLE 78

N-Methyl-N-[2-oxo-2-(4-methylsulfonylphenyl)]ethyl-4-chlorophenacetamide

The procedure was in the same manner as described in Example 75, except that the starting material was N-methyl-N-[2-hydroxy-2-(4-methylsulfonylphenyl)]ethyl-4-chlorophenacetamide instead of N-methyl-N-[2-hydroxy-2-(4-methylsulfonylphenyl)]ethyl-phenacetamide. The title compound was obtained as a yellow solid, Mp. 163–165° C. yield: 34.0%.

$M^+$=379, $C_{18}H_{20}NClO_4S$ $^1$H-NMR: δ8.15–8.05 (dd, 4H, ArH, J=8.7), 7.34–7.19 (m, 4H, ArH), 4.84 (s, 2H, $CH_2$), 3.81 (s, 3H, CH3), 3.14 (s, 3H, CH3), 3.08 (s, 3H, $SO_2CH_3$)

EXAMPLE 79

N-Methyl-N-[2-oxo-2-(4-methylsulfonylphenyl)]ethyl-3-chlorophenacetamide

The procedure was in the same manner as described in example 75, except that the starting material was N-methyl-N-[2-hydroxy-2-(4-methylsulfonylphenyl)]ethyl-3-chlorophenacetamide instead of N-methyl-N-[2-hydroxy-2-(4-methylsulfonylphenyl)]ethyl-phenacetamide. The title compound was obtained as yellow solid, yield: 24.7%.

EXAMPLE 80

N-Methyl-N-[2-oxo-2-(4-methylsulfonylphenyl)]ethyl-4-bromophenacetamide

The procedure was in the same manner as described in example 75, except that the starting material was N-methyl-N-[2-hydroxy-2-(4-methylsulfonylphenyl)]ethyl-4-bromophenacetamide instead of N-methyl-N-[2-hydroxy-2-(4-methylsulfonylphenyl)]ethyl-phenacetamide. The title compound was obtained as a yellow solid, Mp. 156.7–158.1° C., yield: 56.8%, $M^+$=424

$^1$H-NMR: δ8.15–8.05 (dd, 4H, ArH, J=8.7), 7.34–7.19 (m, 4H, ArH), 4.84 (s, 2H, $CH_2$), 3.81 (s, 3H, CH3), 3.14 (s, 3H, CH3), 3.08 (s, 3H, $SO_2CH_3$)

EXAMPLE 81

N-Methyl-N-[2-oxo-2-(4-methylsulfonylphenyl)]ethyl-4-fluorophenacetamide

The procedure was in the same manner as described in example 75, except that the starting material was N-methyl-N-[2-hydroxy-2-(4-methylsulfonylphenyl)]ethyl-4-fluorophenacetamide instead of N-methyl-N-[2-hydroxy-2-(4-methylsulfonylphenyl)]ethyl-phenacetamide. The title compound was obtained as a yellow solid, Mp. 109.3–111.4° C., yield: 37.8%, $M^+$=363

$^1$H-NMR: δ8.14–8.04 (dd, 4H, ArH, J=8.4), 7.29–7.03 (m, 4H, ArH), 4.83 (s, 2H, $CH_2$), 3.81 (s, 2H, CH2), 3.14 (s, 3H, CH3), 3.04 (s, 3H, $SO_2CH_3$), 2.34 (s, 3H, CH3), 1.57–150 (m, 2H, CH2), 0.92–0.87 (t, 3H, CH3)

EXAMPLE 82

N-Propyl-N-[2-oxo-2-(4-methylsulfonylphenyl)]ethyl-3-methylphenacetamide

The procedure was in the same manner as described in example 75, except that the starting material was N-propyl-N-[2-hydroxy-2-(4-methylsulfonylphenyl)]ethyl-3-methylphenacetamide instead of N-methyl-N-[2-hydroxy-2-(4-methylsulfonylphenyl)]ethyl-phenacetamide. The title compound was obtained as a yellow solid, Mp. 129.6–131.0° C., yield: 26.6%, $M^+$=387

$^1$H-NMR: δ8.15–8.02 (dd, 4H, ArH, J=7.8), 7.24–7.06 (m, 4H, ArH), 4.73 (s, 2H, $CH_2$), 3.79 (s, 2H, CH2), 3.40–3.34 (t, 2H, CH2, J=7.8), 3.07 (s, 3H, SO₂CH₃), 2.34 (s, 3H, CH3), 1.57–1.50 (m, 2H, CH2), 0.92–0.87 (t, 3H, CH3)

EXAMPLE 83

N-Propyl-N-[2-oxo-2-(4-methylsulfonylphenyl)]ethyl-4-methylphenacetamide

The procedure was in the same manner as described in example 75, except that the starting material was N-propyl-N-[2-hydroxy-2-(4-methylsulfonylphenyl)]ethyl-4-methylphenacetamide instead of N-methyl-N-[2-hydroxy-2-(4-methylsulfonylphenyl)]ethyl-phenacetamide. The title compound was obtained as a yellow solid, Mp. 129.6–131.0° C., yield: 36.2%, M$^+$=387

$^1$H-NMR: δ8.14–8.02 (dd, 4H, ArH, J=7.8), 7.18–7.12 (m, 4H, ArH), 4.72 (s, 2H, CH₂), 3.77 (s, 2H, CH2), 3.39–3.33 (t, 2H, CH2, J=7.8), 3.07 (s, 3H, SO₂CH₃), 2.33 (s, 3H, CH3), 1.58–1.51 (m, 2H, CH2), 0.92–0.87 (t, 3H, CH3)

EXAMPLE 84

N-Propyl-N-[2-oxo-2-(4-methylsulfonylphenyl)]ethyl-4-fluorolphenacetamide

The procedure was in the same manner as described in example 75, except that the starting material was N-propyl-N-[2-hydroxy-2-(4-methylsulfonylphenyl)]ethyl-4-fluorophenacetamide instead of N-methyl-N-[2-hydroxy-2-(4-methylsulfonylphenyl)]ethyl-phenacetamide. The title compound was obtained as a yellow solid, Mp. 174.5–175.0° C., yield: 40.6%, M$^+$=391

$^1$H-NMR: δ8.15–8.03 (dd, 4H, ArH, J=8.1), 7.28–7.00 (m, 4H, ArH), 4.74 (s, 2H, CH₂), 3.79 (s, 2H, CH2), 3.41–3.35 (t, 2H, CH2, J=7.5), 3.07 (s, 3H, SO₂CH₃), 1.61–1.54 (m, 2H, CH2), 0.94–0.89 (t, 3H, CH3, J=7.5)

EXAMPLE 85

N-Propyl-N-[2-oxo-2-(4-methylsulfonylphenyl)]ethyl-4-chlorophenacetamide

The procedure was in the same manner as described in example 75, except that the starting material was N-propyl-N-[2-hydroxy-2-(4-methylsulfonylphenyl)]ethyl-4-chlorophenacetamide instead of N-methyl-N-[2-hydroxy-2-(4-methylsulfonylphenyl)]ethyl-phenacetamide. The title compound was obtained as a yellow solid, Mp. 133.0–134.0° C., yield: 32.1%, M$^+$=407

$^1$H-NMR: δ8.15–8.02 (dd, 4H, ArH, J=8.7), 7.33–7.21 (dd, 4H, ArH, J=8.1), 4.74 (s, 2H, CH₂), 3.79 (s, 2H, CH2), 3.40–3.34 (t, 2H, CH2, J=7.5), 3.07 (s, 3H, SO₂CH₃), 1.62–1.54 (m, 2H, CH2), 0.95–0.90 (t, 3H, CH3, J=7.5)

EXAMPLE 86

N-Cyclopropyl-N-[2-oxo-2-(4-methylsulfonylphenyl)]ethyl-4-methylphenacetamide

The procedure was in the same manner as described in example 75, except that the starting material was N-cyclopropyl-N-[2-hydroxy-2-(4-methylsulfonylphenyl)]ethyl-4-methylphenacetamide instead of N-methyl-N-[2-hydroxy-2-(4-methylsulfonylphenyl)]ethyl-phenacetamide. The title compound was obtained as a yellow solid, Mp. 109.0–111.0° C., yield: 36.2%, M$^+$=385

$^1$H-NMR: δ8.12–8.02 (dd, 4H, ArH, J=8.4), 7.20–7.12 (m, 4H, ArH), 4.78 (s, 2H, CH₂), 3.97 (s, 2H, CH2), 3.08 (s, 3H, SO2CH3), 2.91–2.84 (m, 1H, CH), 2.33 (s, 3H, CH3), 0.96–0.83 (m, 4H, CH2CH2)

EXAMPLE 87

N-Cyclopropyl-N-[2-oxo-2-(4-methylsulfonylphenyl)]ethyl-3-methylphenacetamide

The procedure was in the same manner as described in example 75, except that the starting material was N-cyclopropyl-N-[2-hydroxy-2-(4-methylsulfonylphenyl)]ethyl-4-methylphenacetamide instead of N-methyl-N-[2-hydroxy-2-(4-methylsulfonylphenyl)]ethyl-phenacetamide. The title compound was obtained as a yellow solid, Mp. 81.0–83.0° C., yield: 52.8%, M$^+$=385

$^1$H-NMR: δ8.13–8.02 (dd, 4H, ArH, J=8.4), 7.24–7.01 (m, 4H, ArH), 4.79 (s, 2H, CH₂), 3.98 (s, 2H, CH2), 3.07 (s, 3H, SO2CH3), 2.92–2.88 (m, 1H, CH), 2.34 (s, 3H, CH3), 0.97–0.84 (m, 4H, CH2CH2)

EXAMPLE 88

N-Cyclohexyl-N-[2-oxo-2-(4-methylsulfonylphenyl)]ethyl-4-chlorophenacetamide

The procedure was in the same manner as described in example 75, except that the starting material was N-cyclohexyl-N-[2-hydroxy-2-(4-methylsulfonylphenyl)]ethyl-4-chlorophenacetamide instead of N-methyl-N-[2-hydroxy-2-(4-methylsulfonylphenyl)]ethyl-phenacetamide. The title compound was obtained as a yellow solid, Mp. 149.1–150.6° C., yield: 15.2%, M$^+$=429

$^1$H-NMR: δ8.16–8.03 (dd, 4H, ArH, J=8.4), 7.34–7.24 (m, 4H, ArH), 4.59 (s, 2H, CH₂), 3.81 (s, 2H, CH2), 3.65–3.61 (m, 1H, CH) 3.07 (s, 3H, SO2CH3), 1.79–1.20, 2.33 (m, 10H, (CH2)5)

EXAMPLE 89

N-Cylcopropyl-N-[2-oxo-2-(4-methylsulfonylphenyl)]ethyl-4-fluorophenacetamide

The procedure was in the same manner as described in example 75, except that the starting material was N-cyclopropyl-N-[2-hydroxy-2-(4-methylsulfonylphenyl)]ethyl-4-fluorophenacetamide instead of N-methyl-N-[2-hydroxy-2-(4-methylsulfonylphenyl)]ethyl-phenacetamide. The title compound was obtained as a yellow solid, Mp. 108.8–110.0° C., yield: 43.1%, M$^+$=389

$^1$H-NMR: δ8.12–8.03 (dd, 4H, ArH, J=8.4), 7.29–6.98 (tt, 4H, ArH), 4.79 (s, 2H, CH₂), 3.98 (s, 2H, CH2), 3.07 (s, 3H, SO2CH3), 3.00–2.90 (m, 1H, CH), 0.96–0.86 (m, 4H, CH2CH2)

EXAMPLE 90

N-Methyl-N-[2-oxo-2-(4-methylsulfonylphenyl)]ethyl-3-methylphenacetamide

The procedure was in the same manner as described in example 75, except that the starting material was N-methyl- N-[2-hydroxy-2-(4-methylsulfonylphenyl)]ethyl-3-methylphenacetamide instead of N-methyl-N-[2-hydroxy-2-(4-methylsulfonylphenyl)]ethyl-phenacetamide. The title compound was obtained as a yellow solid, Mp. 123.8–124.6° C., yield: 47.0%, M$^+$=359

$^1$H-NMR: δ8.15–8.04 (dd, 4H, ArH, J=8.4), 7.23–7.07 (m, 4H, ArH), 4.83 (s, 2H, CH$_2$), 3.80 (s, 2H, CH2), 3.13 (s, 3H, CH3), 3.08 (s, 3, SO$_2$CH$_3$), 2.35 (s, 3H, CH3)

EXAMPLE 91

N-Methyl-N-[2-oxo-2-(4-methylsulfonylphenyl)]ethyl-2,4-dimethylphenacetamide

The procedure was in the same manner as described in example 75, except that the starting material was N-methyl-N-[2-hydroxy-2-(4-methylsulfonylphenyl)]ethyl-2,4-dimethylphenacetamide instead of N-methyl-N-[2-hydroxy-2-(4-methylsulfonylphenyl)]ethyl-phenacetamide. The title compound was obtained as a yellow oily liquid, yield: 46.3%,

EXAMPLE 92

N-Propyl-N-[2-oxo-2-(4-methylsulfonylphenyl)]ethyl-4-phenoxyacetamide

The procedure was in the same manner as described in example 75, except that the starting material was N-propyl-N-[2-hydroxy-2-(4-methylsulfonylphenyl)]ethyl-4-phenoxyacetamide instead of N-methyl-N-[2-hydroxy-2-(4-methylsulfonylphenyl)]ethyl-phenacetamide, The title compound was obtained as a yellow solid, Mp. 96.0–98.0° C., yield: 94.7%, M$^+$=389

$^1$H-NMR: δ8.13–8.00 (dd, 4H, ArH, J=8.1), 7.32–6.93 (m, 5H, ArH), 4.82 (s, 2H, CH$_2$), 4.76 (s, 2H, CH2), 3.45–3.40 (t, 2H, CH2, J=7.5), 3.08 (s, 3H, SO$_2$CH$_3$), 1.69–1.62 (m, 2H, CH2), 0.98–0.93 (t, 3H, CH3, J=7.5)

EXAMPLE 93

N-Propyl-N-[2-oxo-2-(3-bromophenyl)]ethyl-4-aminosulfonylphenacetamide

The procedure was in the same manner as described in example 64, except that the starting material was N-propyl-N-[2-hydroxy-2-(3-bromophenyl)]ethyl-4-aminosulfonyl phenacetamide instead of N-methyl-N-(2-hydroxy-2-phenyl) ethyl-4-methylsulfonyl phenacetamide.

The title compound was obtained as yellow oil, yield 52.0%.

EXAMPLE 94

N-Propyl-N-[2-oxo-2-(3-chlorophenyl)]ethyl-4-aminosulfonylphenacetamide

The procedure was in the same manner as described in example 64, except that the starting material is N-propyl-N-[2-hydroxy-2-(3-chlorophenyl)]ethyl-4-aminosulfonyl phenacetamide instead of N-methyl-N-(2-hydroxy-2-phenyl) ethyl-4-methylsulfonyl phenacetamide. The title compound was obtained as yellow oil, yield 28.1%.

EXAMPLE 95

N-Cycopropyl-N-[2-oxo-2-(4-chlorophenyl)]ethyl-4-aminosulfonylphenacetamide

The procedure was in the same manner as described in example 64, except that the starting material is N-propyl-N-[2-hydroxy-2-(4-chlorophenyl)]ethyl-4-aminosulfonyl phenacetamide instead of N-methyl-N-(2-hydroxy-2-phenyl) ethyl-4-methylsulfonyl phenacetamide. The title compound was obtained as yellow oil, yield 48.7%.

EXAMPLE 96

N-Propyl-N-[2-oxo-2-(3-fluorophenyl)]ethyl-4-aminosulfonylphenacetamide

The procedure was in the same manner as described in example 64, except that the starting material was N-propyl-N-[2-hydroxy-2-(3-fluorophenyl)]ethyl-4-aminosulfonyl phenacetamide instead of N-methyl-N-(2-hydroxy-2-phenyl) ethyl-4-methylsulfonyl phenacetamide. The title compound was obtained as yellow oil, yield 38.7%.

EXAMPLE 97

N-Propyl-N-[2-oxo-2-(4-fluorophenyl)]ethyl-4-aminosulfonylphenacetamide

The procedure was in the same manner as described in example 64, except that the starting material was N-propyl-N-[2-hydroxy-2-(4-chlorophenyl)]ethyl-4-aminosulfonyl phenacetamide instead of N-methyl-N-(2-hydroxy-2-phenyl) ethyl-4-methylsulfonyl phenacetamide. The title compound was obtained as yellow oil, yield 37.8%.

EXAMPLE 98

N-Cycopropyl-N-[2-oxo-2-(3-chlorophenyl)]ethyl-4-aminosulfonylphenacetamide

The procedure was in the same manner as described in example 64, except that the starting material was N-propyl-N-[2-hydroxy-2-(3-chlorophenyl)]ethyl-4-aminosulfonyl phenacetamide instead of N-methyl-N-(2-hydroxy-2-phenyl) ethyl-4-methylsulfonyl phenacetamide. The title compound was obtained as yellow oil, yield 19.1%.

EXAMPLE 99

N-Cycopropyl-N-[2-oxo-2-(4-fluorophenyl)]ethyl-4-aminosulfonylphenacetamide

The procedure was in the same manner as described in example 64, except that the starting material was N-propyl-N-[2-hydroxy-2-(4-fluorophenyl)]ethyl-4-aminosulfonyl phenacetamide instead of N-methyl-N-(2-hydroxy-2-phenyl) ethyl-4-methylsulfonyl phenacetamide. The title compound was obtained as yellow oil, yield 35.9%.

EXAMPLE 100

N-Propyl-N-[2-oxo-2-(3-bromophenyl)]ethyl-4-aminosulfonylphenacetamide

The procedure was in the same manner as described in example 64, except that the starting material was N-propyl- N-[2-hydroxy-2-(3-bromophenyl)]ethyl-4-aminosulfonyl phenacetamide instead of N-methyl-N-(2-hydroxy-2-phenyl) ethyl-4-methylsulfonyl phenacetamide. The title compound was obtained as yellow oil, yield 52.0%.

EXAMPLE 101

N-Cycopropyl-N-[2-oxo-2-(4-methylphenyl)]ethyl-4-aminosulfonylphenacetamide

The procedure was in the same manner as described in example 64, except that the starting material was N-propyl-N-[2-hydroxy-2-(4-methylphenyl)]ethyl-4-aminosulfonyl phenacetamide instead of N-methyl-N-(2-hydroxy-2-phenyl) ethyl-4-methylsulfonyl phenacetamide. The title compound was obtained as yellow oil, yield 39.7%.

EXAMPLE 102

N-Cycopropyl-N-[2-oxo-2-(3-methylphenyl)]ethyl-4-aminosulfonylphenacetamide

The procedure was in the same manner as described in example 64, except that the starting material was N-propyl-N-[2-hydroxy-2-(4-chlorophenyl)]ethyl-4-aminosulfonyl phenacetamide instead of N-methyl-N-(2-hydroxy-2-phenyl) ethyl-4-methylsulfonyl phenacetamide. The title compound was obtained as yellow oil, yield 42.6%.

Preparation of N-alkyl-3,4-diaryl-2,5-dihydropyrrole-2-ones

EXAMPLE 103

N-Methyl-3-(4-methylsulfonylphenyl)-4-phenyl-2,5-dihydropyrrole-2-one

A potassium t-butanolate was prepared by refluxing 0.200 g of potassium in 25 ml of anhydrous t-butanol in a nitrogen atmosphere for 2–4 hours. To the potassium t-butanolate solution was rapidly added a solution of 1 mmol of N-methyl-N-(2-oxo-2-phenyl)ethyl-4-methylsulfonylphenacetamide described in Example 50 in 40 ml of hot t-butanol. The mixture turned to yellow-green in color, and was stirred until the starting material disappeared, as monitored by TLC. The reaction mixture was poured into ice-water and neutralized by adding dilute hydrochloric acid. The mixture was extracted by ethyl acetate. The combined organic phase was washed with water and dried over sodium sulfate. The solvent was evaporated and the residue was purified by column chromatograph on silica gel (eluent: ethyl acetate: petroleum ether 1:2–1) to give the title compound as white solid. Mp. 195° C. (dec), yield: 63.9%.

$M^+$=327. $C_{19}H_{17}ClNO_3S$ $^1$H-NMR: δ8.0–7.7 (dd, 4H, ArH, J=8.4), 7.4–7.2 (m, 2H, ArH), 7.0 (t, 2H, ArH, J=6.6), 4.3 (s, 2H, $CH_2$), 3.1 (s, 3H, $SO_2CH_3$), 3.1 (s, 3H, $NCH_3$)

EXAMPLE 104

N-Propyl-3-(4-methylsulfonylphenyl)-4-(4-methylphenyl)-2,5-dihydropyrrole-2-one

The procedure was in the same manner as described in example 103, except that the starting material was N-propyl-N-[2-oxo-2-(4-methylphenyl)]ethyl-4-methylsulfonylphenacetamide instead of N-methyl-N-(2-oxo-2-phenyl)ethyl-4-methylsulfonylphenacetamide. The title compound was obtained as a white solid, Mp. 155.5–157.6° C., yield: 57.2%.

$M^+$=369 $C_{21}H_{23}NO_3S$ $^1$H-NMR: δ7.9–7.63 (dd, 4H, ArH, J=7.8), 7.13 (s, 4H, ArH), 4.32 (s, 2H, $CH_2$), 3.55 (t, 2H, $NCH_2$, J=7.53), 3.05 (s, 3H, $SOCH_3$), 2.36 (s, 3H, Ar—$CH_3$), 1.75–1.68 (m, 2H, $NCCH_2$) 1.0 (t, $CH_3$, J=7.5)

EXAMPLE 105

N-Methyl-3-(4-methylsulfonylphenyl)-4-(4-methylphenyl)-2,5-dihydropyrrole-2-one

The procedure was in the same manner as described in example 103, except that the starting material was N-methyl-N-[2-oxo-2-(4-methylphenyl)]ethyl-4-methylsulfonylphenacetamide instead of N-methyl-N-(2-oxo-2-phenyl) ethyl-4-methylsulfonylphenacetamide The title compound was obtained as a white solid, Mp. 182.9–185.1° C., yield: 69.2%.

$M^+$=341 $C_{19}H_{19}NO_3S$ $^1$H-NMR: δ7.92–7.61 (dd, 4H, ArH, J=7.8), 7.12 (s, 4H, ArH), 4.33 (s, 2H, $CH_2$), 3.18 (s, 3H, $NCH_3$), 3.06 (s, 3H, $SOCH_3$), 2.36 (s, 3H, Ar—$CH_3$)

EXAMPLE 106

N-Propyl-3-(4-methylsulfonylphenyl)-4-(4-fluorophenyl)-2,5-dihydropyrrole-2-one

The procedure was in the same manner as described in example 103, except that the starting material was N-propyl-N-[2-oxo-2-(4-fluorophenyl)]ethyl-4-methylsulfonylphenacetamide instead of N-methyl-N-(2-oxo-2-phenyl)ethyl-4-methylsulfonylphenacetamide. The title compound was obtained as a white solid, Mp. 150–52° C., yield: 20.9%.

$M^+$=373.0847, $C_{20}H_{20}FNO_3S$ $^1$H-NMR: δ7.93–7.61 (dd, 4H, ArH, J=8.4), 7.24–7.00 (m, 4H, ArH), 4.33 (s, 2H, $CH_2$), 3.58–3.54 (t, $NCH_2$, J=7.2), 3.06 (s, 3H, $SO_2CH_3$), 1.75–1.68 (m, 2H, $NCCH_2$), 1.02–0.97 (t, 3H, $CH_3$)

EXAMPLE 107

N-Cyclopropyl-3-(4-methylsulfonylphenyl)-4-(4-chlorophenyl)-2,5-dihydropyrrole-2-one The procedure was in the same manner as described in example 103, except that the starting material was N-cyclopropyl-N-[2-oxo-2-(4-chlorophenyl)]ethyl-4-methylsulfonylphenacetamide instead of N-methyl-N-(2-oxo-2-phenyl) ethyl-4-methylsulfonylphenacetamide. The title compound was obtained as a white solid, Mp. 107–109° C. (dec), yield: 59.2%.

$M^+$=389.387, $C_{20}H_{18}ClNO_3S$ $^1$H-NMR: δ7.92–7.58 (dd, 4H, ArH, J=8.4), 7.34–7.03 (m, 4H, ArH), 4.27 (s, 2H, $CH_2$), 3.05 (s, 3H, $SO_2CH_3$), 2.88 (m, 1H, NCH), 0.94–0.87 (m, 4H, $CH_2CH_2$)

EXAMPLE 108

N-Cyclopropyl-3-(4-methylsulfonylphenyl)-4-(3-chlorophenyl)-2,5-dihydropyrrole-2-one The procedure was in the same manner as described in example 103, except that the starting material was N-cyclopropyl-N-[2-oxo-2-(3-chlorophenyl)]ethyl-4-methylsulfonylphenacetamide instead of N-methyl-N-(2-oxo-2-phenyl)ethyl-4-methylsulfonylphenacetamide. The title compound was obtained as a white solid, Mp. 158.4–160.1° C. (dec), yield: 53.3%.

M$^+$=389.387, $C_{20}H_{18}ClNO_3S$ $^1$H-NMR: δ7.92–7.58 (dd, 4H, ArH, J=8.4), 7.31–7.14 (dd, 4H, ArH, J=6.3), 4.27 (s, 2H, CH$_2$), 3.05 (s, 3H, SO$_2$CH$_3$), 2.88 (m, 1H, CH), 0.94–0.87 (m, 4H, (CH2)2

EXAMPLE 109

N-Methyl-3-(4-methylsulfonylphenyl)-4-(3-chlorophenyl)-2,5-dihydropyrrole-2-one

The procedure was in the same manner as described in example 103, except that the starting material was N-methyl-N-[2-oxo-2-(3-chlorophenyl)]ethyl-4-methylsulfonylphenacetamide instead of N-methyl-N-(2-oxo-2-phenyl)ethyl-4-methylsulfonylphenacetamide. The title compound was obtained as a white solid, Mp. 170–172.4° C., yield: 47.2%.

M$^+$=361.0539, $C_{18}H_{16}ClNO_3S$ $^1$H-NMR: δ8.04–7.59 (dd, 4H, ArH, J=7.8), 7.35–7.04 (m, 4H, ArH), 4.33 (s, 2H, CH$_2$), 3.19 (s, 3H, NCH$_3$), 3.06 (s, 3H, SO$_2$CH$_3$)

EXAMPLE 110

N-Propyl-3-(4-methylsulfonylphenyl)-4-(3-chlorophenyl)-2,5-dihydropyrrole-2-one

The procedure was in the same manner as described in example 103, except that the starting material was N-Propyl-N-[2-oxo-2-(3-chlorophenyl)]ethyl-4-methylsulfonylphenacetamide instead of N-methyl-N-(2-oxo-2-phenyl)ethyl-4-methylsulfonylphenacetamide. The title compound was obtained as a white solid, Mp. 147.6–149.4° C., yield: 52.6%.

M$^+$=389, $C_{20}H_{20}ClNO_3S$, Elemental analysis Fnd(Cld): C, 61.76 (61.61), H, 5.22 (5.17), N, 3.95 (3.59).

$^1$H-NMR: δ7.99–7.61 (dd, 4H, ArH, J=8.1), 7.35–7.06 (m, 4H, ArH), 4.32 (s, 2H, CH$_2$), 3.56 (t, NCH$_2$, J=7.5), 3.05 (s, 3H, SO$_2$CH$_3$), 1.66 (m, 2H, NCCH$_2$), 1.0–0.97 (t, 3H, CH$_3$, J=7.5)

EXAMPLE 111

N-Methyl-3-(4-methylsulfonylphenyl)-4-(3-bromophenyl)-2,5-dihydropyrrole-2-one

The procedure was in the same manner as described in example 103, except that the starting material was N-methyl-N-[2-oxo-2-(4.bromophenyl)]ethyl-4-methylsulfonylphenacetamide instead of N-methyl-N-(2-oxo-2-phenyl)ethyl-4-methylsulfonylphenacetamide. The title compound was obtained as a white solid, Mp. 137.9–139° C., yield: 71.9%.

M$^+$=407.405, $C_{18}H_{16}BrNO_3S$

Elemental analysis Fnd(Cld): C, 53.48 (53.21), H, 4.15 (3.97), N, 3.48 (3.45).

$^1$H-NMR: δ7.9–7.6 (dd, 4H, ArH, J=8.1), 7.5–7.1 (m, 4H, ArH), 4.3 (s, 2H, CH$_2$), 3.2 (s, 3H, NCH$_3$), 3.1 (s, 3H, SO$_2$CH$_3$); MS: 407, 405

EXAMPLE 112

N-Cyclohexyl-3-(4-methylsulfonylphenyl)-4-phenyl-2,5-dihydropyrrole-2-one

The procedure was in the same manner as described in example 103, except that the starting material was N-cyclohexyl-N-(2-oxo-2-phenyl)ethyl-4-methylsulfonylphenacetamide instead of N-methyl-N-(2-oxo-2-phenyl)ethyl-4-methylsulfonylphenacetamide. The title compound was obtained as a white solid, Mp. 183–185° C., yield: 26.4%.

M$^+$=395.313, $C_{23}H_{25}NO_3S$ $^1$H-NMR: δ7.9–7.6 (dd, 4H, ArH, J=8.1), 7.35–7.22 (m, 5H, ArH), 4.31 (s, 2H, CH$_2$), 4.16 (m, 1H, NCH), 3.05 (s, 3H, SO$_2$CH$_3$), 1.91–1.19 (m, 10H, (CH2)5)

EXAMPLE 113

N-Cyclopropyl-3-(4-methylsulfonylphenyl)-4-(3-fluorophenyl)-2,5-dihydropyrrole-2-one The procedure was in the same manner as described in example 103, except that the starting material was N-cyclopropyl-N-[2-oxo-2-(3-fluorophenyl)]ethyl-4-methylsulfonylphenacetamide instead of N-methyl-N-(2-oxo-2-phenyl)ethyl-4-methylsulfonylphenacetamide. The title compound was obtained as a white solid, Mp. 179–180° C., yield: 47.4%.

M$^+$=371, $C_{20}H_{18}FNO_3S$

Elemental analysis Fnd(Cld): C, 64.57 (64.68), H, 4.86 (4.88), N, 4.01 (3.77).

$^1$H-NMR: δ7.92–7.5 8 (dd, 4H, ArH, J=8.1), 7.31–6.92 (m, 4H, ArH), 4.27 (s, 2H, CH$_2$), 3.06 (s, 3H, SO$_2$CH$_3$), 2.91–2.88 (m, 1H, CH), 0.94–0.89 (m, 4H, (CH2)2)

EXAMPLE 114

N-Methyl-3-phenyl-4-(4-methylsulfonylphenyl)-2,5-dihydropyrrole-2-one

The procedure was in the same manner as described in example 103, except that the starting material was N-methyl-N-[2-oxo-2-(4-methylsulfonylphenyl)]ethyl-4-phenacetamide instead of N-methyl-N-(2-oxo-2-phenyl)ethyl-4-methylsulfonylphenacetamide. The title compound was obtained as a white solid, Mp. 163.4–165.3° C., yield: 48.2%.

M$^+$=327.298, $C_{18}H_{17}NO_3S$ $^1$H-NMR: δ7.87–7.44 (dd, 4H, ArH, J=8.1), 7.36 (s, 5H, ArH), 4.33 (s, 2H, CH$_2$), 3.2 (s, 3H, NCH$_3$), 3.06 (s, 3H, SO$_2$CH$_3$)

EXAMPLE 115

N-Propyl-3-phenyl-4-(4-methylsulfonylphenyl)-2,5-dihydropyrrole-2-one

The procedure was in the same manner as described in example 103, except that the starting material was N-cyclopropyl-N-[2-oxo-2-(4-methylsulfonylphyl)]ethyl-4-phenacetamide instead of N-methyl-N-(2-oxo-2-phenyl)ethyl-4-methylsulfonylphenacetamide. The title compound was obtained as a white solid, Mp. 127.4–12229.0° C., yield: 73.3%.

M+=355.326, $C_{20}H_{21}NO_3S$

¹H-NMR: δ7.8–7.4 (dd, 4H, ArH, J=7.8), 7.34 (s, 5H, ArH), 4.30 (s, 2H, CH₂), 3.47–3.52 (t, 2H, CH2, J=7.2), 3.04 (s, 3H, SO₂CH₃), 1.74–1.66 (m, 2H, CH2), 1.00–0.95 (t, 3H, CH₃, J=7.2)

EXAMPLE 116

N-Cyclopropyl-3-phenyl-4-(4-methylsulfonylphenyl)-2,5-dihydropyrrole-2-one

The procedure was in the same manner as described in example 103, except that the starting material was N-cyclopropyl-N-[2-oxo-2-(4-methylsulfonylphyl)]ethyl-4-phenacetamide instead of N-methyl-N-(2-oxo-2-phenyl)ethyl-4-methylsulfonylphenacetamide The title compound was obtained as a white solid, Mp. 144–146° C., yield: 77.2%.

M+=353.1094, $C_{20}H_{19}NO_3S$

¹H-NMR: δ7.86–7.44 (dd, 4H, ArH, J=8.4), 7.35 (s, 5H, ArH), 4.27 (s, 2H, CH₂), 3.06 (s, 3H, SO₂CH₃), 2.91–2.89 (m, 1H, NCH), 0.94–0.88 (dd, 4H, CH₂CH₂)

EXAMPLE 117

N-Methyl-3-(4-chlorophenyl)-4-(4-methylsulfonylphenyl)-2,5-dihydropyrrole-2-one

The procedure was in the same manner as described in example 103, except that the starting material was N-methyl-N-[2-oxo-2-(4-methylsulfonylphyl)]ethyl-4-chlorophenacetamide instead of N-methyl-N-(2-oxo-2-phenyl)ethyl-4-methylsulfonylphenacetamide. The title compound was obtained as a white solid, Mp. 129–131° C., yield: 76.7%.

M+=3610542, $C_{18}H_{16}NClO_3S$

¹H-NMR: δ7.90–7.44 (dd, 4H, ArH, J=8.7), 7.34–7.16 (m, 4H, ArH), 4.32 (s, 2H, CH₂), 3.20 (s, 3H, NCH₃), 3.08 (s, 3H, SO₂CH₃)

EXAMPLE 118

N-Methyl-3-(3-chlorophenyl)-4-(4-methylsulfonylphenyl)-2,5-dihydropyrrole-2-one

The procedure was in the same manner as described in example 102, except that the starting material was N-methyl-N-[2-oxo-2-(4-methylsulfonylphyl)]ethyl-4-chlorophenacetamide instead of N-methyl-N-(2-oxo-2-phenyl)ethyl-4-methylsulfonylphenacetamide. The title compound was obtained as a white solid, Mp. 168–169.6° C., yield: 58.8%.

M+=361.057, $C_{18}H_{16}NClO_3S$

¹H-NMR: δ7.90–7.4 (dd, 4H, ArH, J=8.4), 7.4–7.2 (m, 4H, ArH), 4.34 (s, 2H, CH₂), 3.2 (s, 3H, NCH₃), 3.08 (s, 3H, SO₂CH₃)

EXAMPLE 119

N-Methyl-3-(4-bromophenyl)-4-(4-methylsulfonylphenyl)-2,5-dihydropyrrole-2-one

The procedure was in the same manner as described in example 103, except that the starting material was N-methyl-N-[2-oxo-2-(4-methylsulfonylphyl)]ethyl-4-bromophenacetamide instead of N-methyl-N-(2-oxo-2-phenyl) ethyl-4-methylsulfonylphenacetamide. The title compound was obtained as a white solid, Mp. 161–163° C., yield: 71.2%.

M+=404.9939, $C_{18}H_{16}NBrO_3S$

¹H-NMR: δ7.90–7.48 (dd, 4H, ArH, J=8.1), 7.46–7.25 (dd, 4H, ArH, J=8.4), 4.32 (s, 2H, CH₂), 3.2 (s, 3H, NCH₃), 3.08 (s, 3H, SO₂CH₃)

EXAMPLE 120

N-Methyl-3-(4-fluorophenyl)-4-(4-methylsulfonylphenyl)-2,5-dihydropyrrole-2-one

The procedure was in the same manner as described in example 103, except that the starting material was N-methyl-N-[2-oxo-2-(4-methylsulfonylphyl)]ethyl-4-fluorophenacetamide instead of N-methyl-N-(2-oxo-2-phenyl) ethyl-4-methylsulfonylphenacetamide. The title compound was obtained as a white solid, Mp. 110.9–111.4° C., yield: 80.4%.

M+=345.0836, $C_{18}H_{16}NFO_3S$

¹H-NMR: δ7.90–7.44 (dd, 4H, ArH, J=8.6), 7.39–7.35 (q, 2H, ArH), 7.08–7.03 (t, 2H, ArH), 4.32 (s, 2H, CH₂), 3.2 (s, 3H, NCH₃), 3.07 (s, 3H, SO₂CH₃)

EXAMPLE 121

N-Propyl-3-(3-methylphenyl)-4-(4-methylsulfonylphenyl)-2,5-dihydropyrrole-2-one

The procedure was in the same manner as described in example 103, except that the starting material was N-propyl-N-[2-oxo-2-(3-methylsulfonylphyl)]ethyl-3-methylphenacetamide instead of N-methyl-N-(2-oxo-2-phenyl)ethyl-4-methylsulfonylphenacetamide. The title compound was obtained as a white solid, Mp. 120–122° C., yield: 45.5%.

M+=369.340, $C_{19}H_{19}NO_3S$

¹H-NMR: δ7.86–7.46 (dd, 4H, ArH, J=7.8), 7.25–7.07 (m, 4H, ArH), 4.32 (s, 2H, CH₂), 3.59–3.54 (t, 2H, CH2), 3.06 (s, 3H, SO₂CH₃), 2.33 (s, 3H, CH3), 1.75–1.65 (m, 2H, CH2), 1.02–0.97 (t, 3H, CH3, J=7.2)

EXAMPLE 122

N-Propyl-3-(4-methylphenyl)-4-(4-methylsulfonylphenyl)-2,5-dihydropyrrole-2-one

The procedure was in the same manner as described in example 103, except that the starting material was N-propyl-N-[2-oxo-2-(4-methylsulfonylphyl)]ethyl-4-methylphenacetamide instead of N-methyl-N-(2-oxo-2-phenyl)ethyl-4-methylsulfonylphenacetamide. The title compound was obtained as a white solid, Mp. 161–163° C., yield: 70.4%.

M+=369.340, $C_{19}H_{19}NO_3S$

¹H-NMR: δ7.87–7.47 (dd, 4H, ArH, J=8.1), 7.29–7.15 (dd, 4H, ArH, J=7.8), 4.30 (s, 2H, CH₂), 3.59–3.54 (t, 2H, CH2, J=7.2), 3.06 (s, 3H, SO₂CH₃), 2.36 (s, 3H, CH3), 1.75–1.68 (m, 2H, CH2), 1.02–0.97 (t, 3H, CH3, J=7.5)

EXAMPLE 123

N-Propyl-3-(4-fluorophenyl)-4-(4-methylsulfonylphenyl)-2,5-dihydropyrrole-2-one

The procedure was in the same manner as described in example 103, except that the starting material was N-propyl-N-[2-oxo-2-(4-methylsulfonylphyl)]ethyl-4-fluorophenacetamide instead of N-methyl-N-(2-oxo-2-phenyl)ethyl-4-methylsulfonylphenacetamide. The title compound was obtained as a white solid, Mp. 120–121° C., yield: 57.7%.

$M^+$=387.373, $C_{18}H_{16}NFO_3S$ $^1$H-NMR: δ7.86–7.43 (dd, 4H, ArH, J=8.4), 7.39–6.99 (m, 4H, ArH), 4.30 (s, 2H, $CH_2$), 3.56–3.51 (t, 2H, CH2, J=7.2), 3.05 (s, 3H, $SO_2CH_3$), 1.76–1.63 (m, 2H, CH2), 1.00–0.95 (t, 3H, CH3, J=7.8)

EXAMPLE 124

N-Propyl-3-(4-chlorophenyl)-4-(4-methylsulfonylphenyl)-2,5-dihydropyrrole-2-one

The procedure was in the same manner as described in example 103, except that the starting material was N-propyl-N-[2-oxo-2-(4-methylsulfonylphyl)]ethyl-4-chlorophenacetamide instead of N-methyl-N-(2-oxo-2-phenyl)ethyl-4-methylsulfonylphenacetamide. The title compound was obtained as a white solid, Mp. 146–148° C., yield: 83.3%.

$M^+$=391.389, $C_{18}H_{16}NClO_3S$

Elemental analysis Fnd(Cld): C, 61.52 (61.61), H, 5.16 (5.17), N, 3.89 (3.59).

$^1$H-NMR: δ7.84–7.42 (dd, 4H, ArH, J=8.4), 7.32–7.24 (broad, 4H, ArH), 4.29 (s, 2H, $CH_2$), 3.54–3.50 (t, 2H, CH2, J=7.2), 3.01 (s, 3H, $SO_2CH_3$), 1.73–1.64 (m, 2H, CH2), 0.97–0.93 (t, 3H, CH3, J=7.2)

EXAMPLE 125

N-Cyclopropyl-3-(4-methylphenyl)-4-(4-methylsulfonylphenyl)-2,5-dihydropyrrole-2-one The procedure was in the same manner as described in example 103, except that the starting material was N-cyclopropyl-N-[2-oxo-2-(4-methylsulfonylphyl)]ethyl-4-(4-methyl)phenacetamide instead of N-methyl-N-(2-oxo-2-phenyl)ethyl-4-methylsulfonylphenacetamide. The title compound was obtained as a white solid, Mp. 214–216° C., yield: 48.3%.

$M^+$=367.338, $C_{21}H_{21}NO_3S$ $^1$H-NMR: δ7.86–7.45 (dd, 4H, ArH, J=8.4), 7.26–7.14 (dd, 4H, ArH, J=8.4), 4.24 (s, 2H, $CH_2$), 3.06 (s, 3H, $SO_2CH_3$), 2.90–2.80 (m, 1H, NCH), 2.36 (s, 3H, CH3), 0.92–0.8 (m, 4H, $CH_2CH_2$)

EXAMPLE 126

N-Cyclopropyl-3-(3-methylphenyl)-4-(4-methylsulfonylphenyl)-2,5-dihydropyrrole-2-one The procedure was in the same manner as described in example 103, except that the starting material was N-cyclopropyl-N-[2-oxo-2-(4-methylsulfonylphyl)]ethyl-3-(3-methyl)phenacetamide instead of N-methyl-N-(2-oxo-2-phenyl)ethyl-4-methylsulfonylphenacetamide. The title compound was obtained as a white solid, Mp. 136.5–137.4° C., yield: 49.0%.

$M^+$=367, $C_{21}H_{21}NO_3S$ $^1$H-NMR: δ7.85–7.44 (dd, 4H, ArH, J=7.8), 7.24–7.05 (m, 4H, ArH), 4.25 (s, 2H, $CH_2$), 3.05 (s, 3H, $SO_2CH_3$), 2.90 (m, 1H, NCH), 2.32 (s, 3H, CH3), 0.89 (m, 4H, $CH_2CH_2$)

EXAMPLE 127

N-Cyclohexyl-3-(4-chlorophenyl)-4-(4-methylsulfonylphenyl)-2,5-dihydropyrrole-2-one The procedure was in the same manner as described in example 103, except that the starting material was N-cyclohexyl-N-[2-oxo-2-(4-methylsulfonylphyl)]ethyl-4-(4-chloro)phenacetamide instead of N-methyl-N-(2-oxo-2-phenyl)ethyl-4-methylsulfonylphenacetamide. The title compound was obtained as a white solid, Mp. 142–143.5° C., yield: 53.7%.

$M^+$=429.347, $C_{23}H_{24}NClO_3S$

Elemental analysis Fnd(Cld): C, 64.41 (64.25), H, 5.57 (5.63), N, 3.50 (3.26).

$^1$H-NMR: δ7.89–7.44 (dd, 4H, ArH, J=8.4), 7.33 (s, 4H, ArH), 4.28 (s, 2H, $CH_2$), 4.16–4.10 (m, 1H, CH), 3.07 (s, 3H, $SO_2CH_3$), 1.91–1.18 (m, 10H, (CH2)5)

EXAMPLE 128

N-Cyclopropyl-3-(4-fluorophenyl)-4-(4-methylsulfonylphenyl)-2,5-dihydropyrrole-2-one The procedure was in the same manner as described in example 103, except that the starting material was N-cyclopropyl-N-[2-oxo-2-(4-methylsulfonylphyl)]ethyl-3-(4-fluorol)phenacetamide instead of N-methyl-N-(2-oxo-2-phenyl)ethyl-4-methylsulfonylphenacetamide. The title compound was obtained as a white solid, Mp. 170.0–172.0° C., yield: 20.0%.

$M^+$=371.183, $C_{20}H_{18}NFO_3S$ $^1$H-NMR: δ7.88–7.43 (dd, 4H, ArH, J=8.4), 7.38–7.01 (m, 4H, ArH), 4.25 (s, 2H, $CH_2$), 3.06 (s, 3H, $SO_2CH_3$), 2.89 (m, 1H, NCH), 0.93–0.87 (m, 4H, $CH_2CH_2$)

EXAMPLE 129

N-Methyl-3-(3-methylphenyl)-4-(4-methylsulfonylphenyl)-2,5-dihydropyrrole-2-one

The procedure was in the same manner as described in example 103, except that the starting material was N-methyl-N-[2-oxo-2-(4-methylsulfonylphyl)]ethyl-4-(3-methyl)phenacetamide instead of N-methyl-N-(2-oxo-2-phenyl)ethyl-4-methylsulfonylphenacetamide. The title compound was obtained as a white solid, Mp. 163.0–165.0° C., yield: 81.1%.

$M^+$=341.312 $C_{19}H_{19}NO_3S$ $^1$H-NMR: δ7.86–7.44 (dd, 4H, ArH, J=7.8), 7.24–7.06 (m, 4H, ArH), 4.32 (s, 2H, $CH_2$), 3.19 (s, 3H, $NCH_3$), 3.05 (s, 3H, $SO_2CH_3$), 2.33 (s, 3H, CH3)

EXAMPLE 130

N-Methyl-3-(2,4-dimethylphenyl)-4-(4-methylsulfonylphenyl)-2,5-dihydropyrrole-2-one The procedure was in the same manner as described in example 103, except that the starting material was N-methyl-N-[2-oxo-2-(4-methylsulfonylphyl)]ethyl-4-(2,4-dimethyl)phenacetamide instead of N-methyl-N-(2-oxo-2-phenyl)ethyl-4-methylsulfonylphenacetamide. The title compound was obtained as a white solid, Mp. 59.0–61° C., yield: 33.4%.

$M^+$=355 $C_{20}H_{21}NO_3S$

¹H-NMR: δ7.81–7.34 (dd, 4H, ArH, J=8.7), 7.07–6.96 (m, 3H, ArH), 4.40 (s, 2H, CH$_2$), 3.18 (s, 3H, NCH$_3$), 3.01 (s, 3H, SO$_2$CH$_3$), 2.34 (s, 3H, CH3), 2.07 (s, 3H, CH3)

EXAMPLE 131

N-Propyl-3-phenoxy-4-(4-methylsulfonylphenyl)-2,5-dihydropyrrole-2-one

The procedure was in the same manner as described in example 103, except that the starting material was N-propyl-N-[2-oxo-2-(4-methylsulfonylphyl)]ethyl-phenoxyacetamide instead of N-methyl-N-(2-oxo-2-phenyl)ethyl-4-methylsulfonylphenacetamide. The title compound was obtained as a white solid, Mp. 163–165° C., yield: 73.1%.

M$^+$=371, C$_{20}$H$_{21}$NO$_4$S

¹H-NMR: δ7.96–7.85 (dd, 4H, ArH, J=8.4), 7.34–7.03 (m, 5H, ArH), 4.35 (s, 2H, CH$_2$), 3.53–3.48 (t, 2H, CH2, J=7.2), 3.05 (s, 3H, SO$_2$CH$_3$), 1.74–1.66 (m, 2H, CH2), 1.00–0.94 (t, 3H, CH3, J=7.2)

EXAMPLE 132

N-Propyl-3-(4-aminosulfonylphenyl)-4-(3-bromophenyl)-2,5-dihydropyrrole-2-one

The procedure was in the same manner as described in example 103, except that the starting material was N-propyl-N-[2-oxo-2-(3-bromophenyl)]ethyl-4-aminosulfonylphenacetamide instead of N-methyl-N-(2-oxo-2-phenyl)ethyl-4-methylsulfonylphenacetamide. The title compound was obtained as a white solid, Mp. 162.5–163.0° C., yield: 77.0%.

M$^+$=435.437 C$_{19}$H$_{19}$N$_2$O$_3$SBrS

¹H-NMR: δ7.90–7.57 (dd, 4H, ArH, J=8.1), 7.50–7.11 (m, 4H, ArH), 4.32 (s, 2H, CH$_2$), 3.58–3.53 (t, 2H, NCH$_2$, J=7.5), 1.78–1.61 (m, 2H, NCCH$_2$), 1.02–0.97 (t, 3H, NCCCH$_3$, J=7.5)

EXAMPLE 133

N-Propyl-3-(4-aminosulfonylphenyl)-4-(3-chlorophenyl)-2,5-dihydropyrrole-2-one

The procedure was in the same manner as described in example 103, except that the starting material was N-Propyl-N-[2-oxo-2-(3-chlorophenyl)]ethyl-4-aminosulfonylphenacetamide instead of N-methyl-N-(2-oxo-2-phenyl)ethyl-4-methylsulfonylphenacetamide. The title compound was obtained as a white solid, Mp. 149–150° C., yield: 43.0%.

M$^+$=390.361, C$_{18}$H$_{19}$ClNO$_3$S

Elemental analysis Fnd(Cld): C, 58.36 (58.40), H, 5.26 (4.90), N, 6.95 (7.17).

¹H-NMR: δ7.9–7.44 (dd, 4H, ArH, J=8.7), 7.3–7.1 (m, 4H, ArH), 4.90 (s, 2H, NH$_3$), 4.3 (s, 2H, CH$_2$), 3.6 (t, NCH$_2$, J=7.8), 1.8–1.7 (m, 2H, NCCH$_2$), 1.0 (t, 3H, CH$_3$, J=7.8)

EXAMPLE 134

N-Cylcopropyl-3-(4-aminosulfonylphenyl)-4-(4-chlorophenyl)-2,5-dihydropyrrole-2-one The procedure was in the same manner as described in example 103, except that the starting material was N-Cycopropyl-N-[2-oxo-2-(4-chlorophenyl)]ethyl-4-aminosulfonylphenacetamide instead of N-methyl-N-(2-oxo-2-phenyl)ethyl-4-methylsulfonylphenacetamide. The title compound was obtained as a white solid, Mp. 198.4–200° C., yield: 16.1%.

M$^+$=391.362, C$_{19}$H$_{17}$ClNO$_3$S

¹H-NMR: δ8.11–7.96 (dd, 4H, ArH, J=8.1), 7.79–7.60 (dd, 4H, ArH, J=7.8), 5.08 (s, 2H, NH$_3$), 3.02 (m, 1H, CH), 0.54 (m, 2H, CH$_2$CH$_2$)

EXAMPLE 135

N-Propyl-3-(4-aminosulfonylphenyl)-4-(3-fluorophenyl)-2,5-dihydropyrrole-2-one

The procedure was in the same manner as described in example 103, except that the starting material was N-Propyl-N-[2-oxo-2-(3-fluorophenyl)]ethyl-4-aminosulfonylphenacetamide instead of N-methyl-N-(2-oxo-2-phenyl)ethyl-4-methylsulfonylphenacetamide. The title compound was obtained as a white solid, Mp. 188.5–190.4° C., yield: 44.4%.

M$^+$=374.345 C$_{18}$H$_{19}$FNO$_3$S

¹H-NMR: δ7.91–7.56 (dd, 4H, ArH, J=8.1), 7.33–6.95 (m, 4H, ArH), 4.32 (s, 2H, CH$_2$), 3.59–3.54 (t, NCH$_2$, J=7.5), 1.78–1.68 (m, 2H, NCCH$_2$), 1.03–0.98 (t, 3H, CH$_3$, J=7.2)

EXAMPLE 136

N-Propyl-3-(4-aminosulfonylphenyl)-4-(4-fluorophenyl)-2,5-dihydropyrrole-2-one

The procedure was in the same manner as described in example 103, except that the starting material was N-Propyl-N-[2-oxo-2-(4-fluorophenyl)]ethyl-4-aminosulfonylphenacetamide instead of N-methyl-N-(2-oxo-2-phenyl)ethyl-4-methylsulfonylphenacetamide. The title compound was obtained as a white solid, Mp. 179.5–181° C., yield: 77.3%.

M$^+$=374.345 C$_{18}$H$_{19}$FNO$_3$S

Elemental analysis Fnd(Cld): C, 61.08 (60.95), H, 5.13 (5.11), N, 7.29 (7.48).

¹H-NMR: δ7.86–7.53 (dd, 4H, ArH, J=8.7), 7.46–7.11 (m, 4H, ArH), 4.48 (s, 2H, CH$_2$), 3.53–3.48 (t, NCH$_2$, J=7.2), 1.71–1.68 (m, 2H, NCH$_2$), 0.96–0.92 (t, 3H, CH$_3$, J=7.2)

EXAMPLE 137

N-Cylcopropyl-3-(4-aminosulfonylphenyl)-4-(3-chlorophenyl)-2,5-dihydropyrrole-2-one The procedure was in the same manner as described in example 103, except that the starting material was N-Cycopropyl-N-[2-oxo-2-(3-chlorophenyl)]ethyl-4-aminosulfonylphenacetamide instead of N-methyl-N-(2-oxo-2-phenyl)ethyl-4-methylsulfonylphenacetamide. The title compound was obtained as a white solid, Mp. 211–213° C., yield: 62.0%.

M$^+$=402, C$_{19}$H$_{17}$ClNO$_3$S

¹H-NMR: δ7.80–7.44 (dd, 4H, ArH, J=7.8), 7.41–7.15 (m, 4H, ArH), 4.45 (s, 2H, NH$_3$), 2.90–2.88 (m, 1H, CH), 0.86–0.76 (m, 4H, CH$_2$CH$_2$)

EXAMPLE 138

N-Cylcopropyl-3-(4-aminosulfonylphenyl)-4-(4-fluorophenyl)-2,5-dihydropyrrole-2-one The procedure was in the same manner as described in example 103, except that the starting material was N-Cycopropyl-N-[2-oxo-2-(4-fluorophenyl)]ethyl-4-aminosulfonylphenacetamide instead of N-methyl-N-(2-oxo-2-phenyl)ethyl-4-methylsulfonylphenacetamide. The title compound was obtained as a white solid, Mp. 222.8–224.1° C., yield: 41.6%.

$M^+$=372, $C_{19}H_{17}FNO_3S$ $^1$H-NMR: δ7.86–7.50 (dd, 4H, ArH, J=8.4), 7.43–7.10 (m, 4H, ArH), 4.40 (s, 2H, $NH_3$), 2.92–2.87 (m, 1H, CH), 0.91–0.77 (m, 4H, $CH_2CH_2$)

EXAMPLE 139

N-Cylcopropyl-3-(4-aminosulfonylphenyl)-4-(3-bromophenyl-2,5-dihydropyrrole-2-one The procedure was in the same manner as described in example 103, except that the starting material was N-Cycopropyl-N-[2-oxo-2-(3-bromophenyl)]ethyl-4-aminosulfonylphenacetamide instead of N-methyl-N-(2-oxo-2-phenyl)ethyl-4-methylsulfonylphenacetamide. The title compound was obtained as a white solid, Mp. 219–220.4° C., yield: 62.5%.

$M^+$=434, $C_{19}H_{17}BrNO_3S$

Elemental analysis Fnd(Cld): C, 52.43 (52.67), H, 3.70 (3.95), N, 6.33 (6.46).

$^1$H-NMR: δ7.86–7.52 (dd, 4H, ArH, J=8.4), 7.58–7.27 (m, 4H, ArH), 4.41 (s, 2H, CH2), 2.94–2.88 (m, 1H, CH), 0.91–0.78 (m, 4H, $CH_2CH_2$)

EXAMPLE 140

N-Cylcopropyl-3-(4-methylphenyl)-4-(4-aminosulfonylphenyl)-2,5-dihydropyrrole-2-one The procedure was in the same manner as described in example 103, except that the starting material was N-Cycopropyl-N-[2-oxo-2-(4-methylphenyl)]ethyl-4-aminosulfonylphenacetamide instead of N-methyl-N-(2-oxo-2-phenyl)ethyl-4-methylsulfonylphenacetamide. The title compound was obtained as a white solid, Mp. 180.0–182.7° C., yield: 74.7%.

$M^+$=368, $C_{20}H_{20}NO_3S$ $^1$H-NMR: δ8.19–7.95 (dd, 4H, ArH, J=8.4), 7.46–7.22 (dd, 4H, ArH, J=7.8), 4.98 (s, 2H, CH2), 2.97 (m, 1H, CH), 2.29 (s, 3H, CH3), 0.50–0.45 (m, 4H, $CH_2CH_2$)

EXAMPLE 141

N-Cylcopropyl-3-(3-methylphenyl)-4-(4-aminosulfonylphenyl)-2,5-dihydropyrrole-2-one The procedure was in the same manner as described in example 103, except that the starting material was N-Cycopropyl-N-[2-oxo-2-(3-methylphenyl)]ethyl-4-aminosulfonylphenacetamide instead of N-methyl-N-(2-oxo-2-phenyl)ethyl-4-methylsulfonylphenacetamide. The title compound was obtained as a white solid, Mp. 206.0–208.0° C., yield: 37.6%.

$M^+$=368, $C_{20}H_{20}NO_3S$ $^1$H-NMR: δ7.82–7.48 (dd, 4H, ArH, J=8.7), 7.34–7.06 (m, 4H, ArH), 4.40 (s, 2H, CH2), 2.84 (m, 1H, CH), 2.28 (s, 3H, CH3), 0.97–0.77 (m, 4H, $CH_2CH_2$)

PHARMACOLOGICAL EXPERIMENT

1. In vitro Test of Inhibitory Activity for Cyclooxygenase-2 and Cyclooxygenase-1

Cell culture: Adherent macrophages were harvested from the peritoneal cells of male mice (C57BL-6J, Level 2, from Experiment Animal Center, Academy of Military Medical Science) 3 d after the injection (ip) of brewer thioglycollate medium (5 mL/100 g body weight). Shortly, peritoneal cells obtained from 3~4 mice were mixed and seeded in 48 well cell culture cluster (Costar) at a cell density of $1\times10^9$ cell/L in RPMI-1640 supplemented with 5% (v/v) newborn calf serum, 100 ku/L penicillin and 100 g/L streptomycin. After settlement for 2~3 h, non-adherent cells were washed by D-Hanks' balanced salt solution. Then macrophages were cultured in RPMI-1640 without serum. Almost all of adherent cells were macrophages as assessed by Giemsa staining. Cell viability was examined by trypan blue dye exclusion. All incubation procedures were performed with 5% $CO_2$ in humidified air at 37° C.

COX-2 assay: Macrophages were incubated with test compound at different concentrations or solvent ($Me_2SO$) for 1 h and were stimulated with LPS 1 mg/L for 9 h. The amount of $PGE_2$ in supernatants was measured by RIA. The inhibitory ratio was calculated using the same formula as in COX-1 assay section. Cs, Ct, Cc refer to $PGE_2$ concentration in supernatants of LPS, test compound, and control groups, respectively.

COX-1: assay Macrophages were incubated with test compound at different concentrations or solvent ($Me_2SO$) for 1 h and were stimulated with calcimycin 1 μmol·$L^{-1}$ for 1 h. The amount of 6-keto-$PGF_{1\alpha}$ (a stable metabolite of $PGI_2$) in supernatants was measured by RIA according to manufacturer's guide. The inhibitory ratio was calculated as $$IR = \frac{(Cs - Ct)}{(Cs - Cc)}$$

Cs, Ct, Cc refer to 6-keto-$PGF_{1\alpha}$ concentration in supernatants of calcimycin, test compound, and control groups, respectively.

Statistical analysis: Data were expressed as the mean±SD of more than three independent experiments. Dose-inhibitory effect curves were fit through "uphill dose response curves, variable slope" using Prism, GraphPad version3.00:

$$Y = \frac{1}{1 + 10^{[(\log IC_{50} - X) \times Hillslope]}}$$

The inhibitory activities of the compounds of present invention for COX-2 and COX-1 in cell culture are listed in Table 1 below.

TABLE 1

Data of the inhibitory activity of the compounds for COX-2 and COX-1

| Example No | IC$_{50}$ COX-2 (M) | IC$_{50}$ COX-1 (M) | COX-1/COX-2 |
|---|---|---|---|
| 104 | n.d. | n.d. | |
| 105 | 7.82E−7 | >1.0E−5 | |
| 106 | 6.11E−7 | >1.0E−5 | |
| 107 | 4.21E−7 | >1.0E−5 | |
| 108 | 7.83E−7 | >1.0E−5 | |
| 109 | 4.21E−7 | >1.0E−5 | |
| 110 | 7.83E−7 | >1.0E−5 | |
| 111 | 6.19E−7 | >1.0E−S | |
| 112 | 1.79E−6 | >1.0E−5 | |
| 113 | 9.98E−7 | >1.0E−5 | |
| 114 | 1.42E−8 | 1.12E−6 | 78.9 |
| 115 | 1.95E−8 | 1.49E−7 | 7.6 |
| 116 | 2.53E−8 | 4.68E−7 | 18.5 |
| 117 | 2.42E−8 | 1.59E−7 | 6.6 |
| 118 | 1.03E−8 | >1.0E−5 | |
| 119 | 1.18E−8 | 5.72E−8 | 4.9 |
| 120 | 1.38E−8 | 2.00E−7 | 14.5 |
| 121 | 1.93E−8 | 1.19E−7 | 6.2 |
| 122 | 1.50E−8 | 9.13E−8 | 6.1 |
| 123 | 2.86E−8 | 5.02E−7 | 17.6 |
| 124 | 2.45E−8 | 8.02E−9 | |
| 125 | 9.48E−8 | 2.36E−7 | 2.5 |
| 126 | 1.55E−8 | 2.21E−7 | 14.3 |
| 127 | 2.07E−8 | 1.43E−7 | |
| 128 | 6.64E−8 | >1.0E−5 | |
| 129 | n.d. | n.d. | |
| 130 | n.d. | n.d. | |
| 131 | n.d. | n.d. | |
| 132 | 9.98E−7 | >1.0E−5 | |
| 133 | 4.82E−7 | 5.44E8 | |
| 134 | n.d. | n.d. | |
| 135 | 5.64E−7 | >1.0E−5 | |
| 136 | n.d. | n.d. | |
| 137 | 1.69E−6 | >1.0E−5 | |
| 138 | n.d. | n.d. | |
| 139 | n.d. | n.d. | |
| 140 | n.d. | n.d. | |
| 141 | 1.87E−8 | >1.0E−5 | |
| Rofecoxib | 9.57E−9 | >1.0E−5 | |

2. In vitro Test of Inhibitory Activity for Cyclooxygenase-1

Rat Carrageenan-induced Foot Pad Edema Assay

Male Sprgue-Dawley rats (190–220 g) were fasted with free access to water at least 16 h prior to experiments. The rats were dosed orally with a 1 ml suspension of test compound in vehicle (0.5% methyl cellulose and 0.025% Tween-20) or with vehicle alone. One hour later a subplantar injection of 0.1 ml of 1% solution of caarageenan in 0.9% strile saline was administered to the right hind foot pad. Paw volume was measured with a displacement plethysmometer 2, 3, and 4 h after caarageenan injection. The results are listed in Table 2 below.

TABLE 2

Data of inhibitory activity of the compounds for rat carrageenan-induced foot pad edema

| Compound Example No | Dose Mg/kg | Animal No | Paw volumes and the inhibitory percentage of edema ( ) hr | | |
|---|---|---|---|---|---|
| | | | 2 | 3 | 4 |
| control | vehicle | 8 | 45.5 ± 12.9 | 45.5 ± 12.9 | 45.5 ± 12.9 |
| 104 | 10 | 8 | 44.1 ± 6.4 | 46.2 ± 13.7 (24.5%) | 48.6 ± 16.5 (19.3%) |
| 105 | 10 | 8 | 31.0 ± 17.9 | 37.2 ± 9.6 (39.2%) | 31.2 ± 10.7 (48.2%) |
| 108 | 10 | 8 | 38.8 ± 9.8 | 38.9 ± 11.9 (36.4%) | 34.0 ± 12.4 (43.5%) |
| 110 | 10 | 8 | 40.8 ± 8.8 | 45.4 ± 19.4 (25.8%) | 38.1 ± 12.4 (36.7%) |
| 115 | 10 | 8 | 46.4 ± 7.0 | 47.2 ± 13.3 (22.8%) | 43.8 ± 14.5 (27.2%) |
| 117 | 10 | 8 | 22.9 ± 5.9 | 31.7 ± 13.9 (48.2%) | 24.5 ± 7.9 (59.3%) |
| 119 | 10 | 8 | 33.8 ± 17.1 | 31.8 ± 10.8 (48.0%) | 30.2 ± 10.9 (49.8%) |
| 120 | 10 | 8 | 28.9 ± 9.6 | 37.2 ± 20.0 (39.2%) | 44.4 ± 21.5 (26.2%) |
| 122 | 10 | 8 | 33.2 ± 14.2 | 26.2 ± 9.8 (57.2%) | 24.5 ± 14.8 (59.3%) |
| 123 | 10 | 8 | 29.5 ± 14.8 | 30.9 ± 9.9 (49.6%) | 29.9 ± 9.4 (50.3%) |
| 124 | 10 | 8 | 32.5 ± 11.4 | 37.1 ± 12.7 (39.4%) | 40.5 ± 5.4 (32.7%) |
| 125 | 10 | 8 | 35.5 ± 20.0 | 40.3 ± 18.5 (34.1%) | 41.5 ± 12.5 (31.1%) |
| Rofecoxib | 10 | 8 | 42.7 ± 16.9 | 33.1 ± 5.2 (45.9%) | 30.0 ± 1.8 (50.2%) |

The invention claimed is:

1. A sulfonyl-containing 3,4-diaryl-3-pyrrolin-2-ones compound having the formula (I)

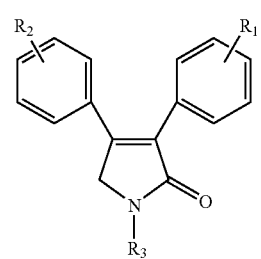

wherein $R_1$ is selected from the group consisting of 4-methylsulfonyl, 4-aminosulfonyl, hydrogen, 2-, 3-, or 4-halogen, $C_1$–$C_6$-alkyl, cyclopentyl, cyclohexyl, $C_1$–$C_4$-alkoxy, hydroxy, cyano, nitro, amino and trifluoromethyl;

$R_2$ is selected from the group consisting of 4-methylsulfonyl, 4-aminosulfonyl, hydrogen, 2-, 3-, or 4-halogen, C1–C6-alkyl, cyclopentyl, cyclohexyl, $C_1$–$C_4$-alkoxy, hydroxy, cyano, nitro, amino and trifluoromethyl; and $R_3$ is selected from the group consisting of hydrogen, methyl, ethyl, n-propyl, i-propyl, c-propyl, n-butyl, isobutyl; provided that when $R_1$ is a methylsulfonyl or aminosulfonyl group, $R_2$ is any group as defined above except a methylsulfonyl or aminosulfonyl group; and when $R_2$ is a methylsulfonyl or aminosulfonyl group, $R_1$ is any group as defined above except a methylsulfonyl or aminosulfonyl group;

with the further proviso that at least one of $R_1$ or $R_2$ is selected from either a methylsulfonyl group or an aminosulfonyl group.

2. The compound of claim 1, wherein the halogen is selected from F, Cl or Br.

3. The compound of claim 1, wherein the alkyl of $R_1$ is a methyl or ethyl group.

4. The compound of claim 1, wherein the alkoxy of $R_1$ is a methoxy group.

5. The compound of claim 1, wherein the alkyl of $R_2$ is a methyl or ethyl group.

6. The compound of claim 1, wherein the alkoxy of $R_2$ is a methoxy group.

7. The compound of claim 1, wherein $R_3$ is selected from hydrogen, methyl, ethyl, n-propyl, i-propyl or cyclo-propyl.

8. The compound of claim 1, wherein the compound is selected from the group consisting of N-methyl-3-(4-methylsulfonylphenyl)-4-(4-phenyl)-2,5-dihydropyrrole-2-one;
N-methyl-3-(4-methylsulfonylphenyl)-4-(4-chlorophenyl)-2,5-dihydropyrrole-2-one;
N-methyl-3-(4-methylsulfonylphenyl)-4-(4-fluorophenyl)-2,5-dihydropyrrole-2-one;
N-propyl-3-(4-methylsulfonylphenyl)-4-(4-chlorophenyl)-2,5-dihydropyrrole-2-one;
N-methyl-3-(4-aminosulfonylphenyl)-4-(4-phenyl)-2,5-dihydropyrrole-2-one;
N-propyl-3-(4-aminosulfonylphenyl)-4-(4-chlorophenyl)-2,5-dihydropyrrole-2-one;
N-propyl-3-(4-methylsulfonylphenyl)-4-(4-methylphenyl)-2,5-dihydropyrrole-2-one;
N-methyl-3-(4-methylsulfonylphenyl)-4-(4-methylphenyl)-2,5-dihydropyrrole-2-one;
N-propyl-3-(4-methylsulfonylphenyl)-4-(4-fluorophenyl)-2,5-dihydropyrrole-2-one;
N-cyclopropyl-3-(4-methylsulfonylphenyl)-4-(4-chlorophenyl)-2,5-dihydropyrrole-2-one;
N-methyl-3-(4-methylsulfonylphenyl)-4-(3-chlorophenyl)-2,5-dihydropyrrole-2-one;
N-propyl-3-(4-methylsulfonylphenyl)-4-(3-chlorophenyl)-2,5-dihydropyrrole-2-one;
N-methyl-3-(4-methylsulfonylphenyl)-4-(4-bromophenyl)-2,5-dihydropyrrole-2-one;
N-methyl-3-phenyl-4-(4-methylsulfonylphenyl)-2,5-dihydropyrrole-2-one;
N-cyclopropyl-3-phenyl-4-(4-methylsulfonylphenyl)-2,5-dihydropyrrole-2-one;
N-methyl-3-(4-chlorophenyl)-4-(4-methylsulfonylphenyl)-2,5-dihydropyrrole-2-one;
N-methyl-3-(3-chlorophenyl)-4-(4-methylsulfonylphenyl)-2,5-dihydropyrrole-2-one;
N-methyl-3-(4-bromophenyl)-4-(4-methylsulfonylphenyl)-2,5-dihydropyrrole-2-one;
N-methyl-3-(4-fluorophenyl)-4-(4-methylsulfonylphenyl-2,5-dihydropyrrole-2-one;
N-propyl-3-(4-aminosulfonylphenyl)-4-(3-chlorophenyl)-2,5-dihydropyrrole-2-one;
N-propyl-3-(4-aminosulfonylphenyl)-4-(3-bromophenyl)-2,5-dihydropyrrole-2-one;
N-cyclopropyl-3-(4-aminosulfonylphenyl)-4-(3-chlorophenyl)-2,5-dihydropyrrole-2-one;
N-Propyl-3-(4-methylsulfonylphenyl)-4-(4-methylphenyl)-2,5-dihydropyrrole-2-one;
N-Cyclopropyl-3-(4-methylsulfonylphenyl)-4-(3-chlorophenyl)-2,5-dihydropyrrole-2-one;
N-Cyclohexyl-3-(4-methylsulfonylphenyl)-4-phenyl-2,5-dihydropyrrole-2-one;
N-Cyclopropyl-3-(4-methylsulfonylphenyl)-4-(3-fluorophenyl)-2,5-dihydropyrrole-2-one;
N-Propyl-3-phenyl-4-(4-methylsulfonylphenyl)-2,5-dihydropyrrole-2-one;
N-Methyl-3-(3-chlorophenyl)-4-(4-methylsulfonylphenyl)-2,5-dihydropyrrole-2-one;
N-Propyl-3-(3-methylphenyl)-4-(4-methylsulfonylphenyl)-2,5-dihydropyrrole-2-one;
N-Propyl-3-(4-methylphenyl)-4-(4-methylsulfonylphenyl)-2,5-dihydropyrrole-2-one;
N-Propyl-3-(4-fluorophenyl)-4-(4-methylsulfonylphenyl)-2,5-dihydropyrrole-2-one;
N-Propyl-3-(4-chlorophenyl)-4-(4-methylsulfonylphenyl)-2,5-dihydropyrrole-2-one;
N-Cyclopropyl-3-(4-methylphenyl)-4-(4-methylsulfonylphenyl)-2,5-dihydropyrrole-2-one;
N-Cyclopropyl-3-(3-methylphenyl)-4-(4-methylsulfonylphenyl)-2,5-dihydropyrrole-2-one;
N-Cyclohexyl-3-(4-chlorophenyl)-4-(4-methylsulfonylphenyl)-2,5-dihydropyrrole-2-one;
N-Cyclopropyl-3-(4-fluorophenyl)-4-(4-methylsulfonylphenyl)-2,5-dihydropyrrole-2-one;
N-Methyl-3-(3-methylphenyl)-4-(4-methylsulfonylphenyl)-2,5-dihydropyrrole-2-one;
N-Methyl-3-(2,4-dimethylphenyl)-4-(4-methylsulfonylphenyl)-2,5-dihydropyrrole-2-one;
N-Propyl-3-phenoxy-4-(4-methylsulfonylphenyl)-2,5-dihydropyrrole-2-one;
N-Propyl-3-(4-aminosulfonylphenyl)-4-(3-bromophenyl)-2,5-dihydropyrrole-2-one;
N-Propyl-3-(4-aminosulfonylphenyl)-4-(3-chlorophenyl)-2,5-dihydropyrrole-2-one;
N-Cyclopropyl-3-(4-aminosulfonylphenyl)-4-(4-chlorophenyl)-2,5-dihydropyrrole-2-one;
N-Propyl-3-(4-aminosulfonylphenyl)-4-(3-fluorophenyl)-2,5-dihydropyrrole-2-one;
N-Propyl-3-(4-aminosulfonylphenyl)-4-(4-fluorophenyl)-2,5-dihydropyrrole-2-one;
N-Cyclopropyl-3-(4-aminosulfonylphenyl)-4-(4-fluorophenyl)-2,5-dihydropyrrole-2-one;
N-Cyclopropyl-3-(4-aminosulfonylphenyl)-4-(3-bromophenyl)-2,5-dihydropyrrole-2-one;
N-Cyclopropyl-3-(4-methylphenyl)-4-(4-aminosulfonylphenyl)-2,5-dihydropyrrole-2-one; and
N-Cyclopropyl-3-(3-methylphenyl)-4-(4-aminosulfonylphenyl)-2,5-dihydropyrrole-2-one.

9. The compound of claim 1, wherein the compound is N-methyl-3-(4-methylsulfonylphenyl)-4-(4-chlorophenyl)-2,5-dihydropyrrole-2-one.

10. The compound of claim 1, wherein the compound is N-methyl-3-(4-methylsulfonylphenyl)-4-(4-fluorophenyl)-2,5-dihydropyrrole-2-one.

11. The compound of claim 1, wherein the compound is N-propyl-3-(4-methylsulfonylphenyl)-4-(4-chlorophenyl)-2,5-dihydropyrrole-2-one.

12. The compound of claim 1, wherein the compound is N-methyl-3-(4-aminosulfonylphenyl)-4-(4-phenyl)-2,5-dihydropyrrole-2-one.

13. The compound of claim 1, wherein the compound is N-propyl-3-(4-aminosulfonylphenyl)-4-(4-chlorophenyl)-2,5-dihydropyrrole-2-one.

14. The compound of claim 1, wherein the compound is N-propyl-3-(4-methylsulfonylphenyl)-4-(4-methylphenyl)-2,5-dihydropyrrole-2-one.

15. The compound of claim 1, wherein the compound is N-methyl-3-(4-methylsulfonylphenyl)-4-(4-methylphenyl)-2,5-dihydropyrrole-2-one.

16. The compound of claim 1, wherein the compound is N-propyl-3-(4-methylsulfonylphenyl)-4-(4-fluorophenyl)-2,5-dihydropyrrole-2-one.

17. The compound of claim 1, wherein the compound is N-cyclopropyl-3-(4-methylsulfonylphenyl)-4-(4-chlorophenyl)-2,5-dihydropyrrole-2-one.

18. The compound of claim 1, wherein the compound is N-methyl-3-(4-methylsulfonylphenyl)-4-(3-chlorophenyl)-2,5-dihydropyrrole-2-one.

19. The compound of claim 1, wherein the compound is N-propyl-3-(4-methylsulfonylphenyl)-4-(3-chlorophenyl)-2,5-dihydropyrrole-2-one.

20. The compound of claim 1, wherein the compound is N-methyl-3-(4-methylsulfonylphenyl)-4-(4-bromophenyl)-2,5-dihydropyrrole-2-one.

21. The compound of claim 1, wherein the compound is N-methyl-3-phenyl-4-(4-methylsulfonylphenyl)-2,5-dihydropyrrole-2-one.

22. The compound of claim 1, wherein the compound is N-cyclopropyl-3-phenyl-4-(4-methylsulfonylphenyl)-2,5-dihydropyrrole-2-one.

23. The compound of claim 1, wherein the compound is N-methyl-3-(4-chlorophenyl)-4-(4-methylsulfonylphenyl)-2,5-dihydropyrrole-2-one.

24. The compound of claim 1, wherein the compound is N-methyl-3-(3-chlorophenyl)-4-(4-methylsulfonylphenyl)-2,5-dihydropyrrole-2-one.

25. The compound of claim 1, wherein the compound is N-methyl-3-(4-bromophenyl)-4-(4-methylsulfonylphenyl)-2,5-dihydropyrrole-2-one.

26. The compound of claim 1, wherein the compound is N-methyl-3-(4-fluorophenyl)-4-(4-methylsulfonylphenyl)-2,5-dihydropyrrole-2-one.

27. The compound of claim 1, wherein the compound is N-propyl-3-(4-aminosulfonylphenyl)-4-(3-chlorophenyl)-2,5-dihydropyrrole-2-one.

28. The compound of claim 1, wherein the compound is N-propyl-3-(4-aminosulfonylphenyl)-4-(3-bromophenyl)-2,5-dihydropyrrole-2-one.

29. The compound of claim 1, wherein the compound is N-cyclopropyl-3-(4-aminosulfonylphenyl)-4-(3-chlorophenyl)-2,5-dihydropyrrole-2-one.

30. A pharmaceutical composition consisting essentially of a therapeutically effective amount of a compound according to claim 1 and at least one pharmaceutically acceptable carrier.

31. A process for preparing a sulfonyl-containing 3,4-diaryl-3-pyrrolin-2-ones compound having the formula (I),

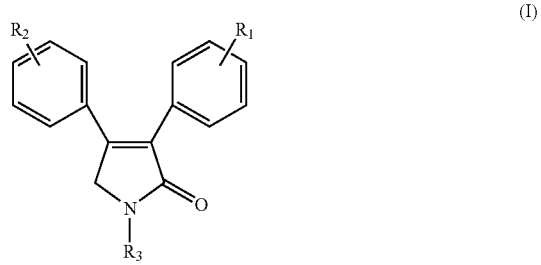

wherein $R_1$ is selected from the group consisting of 4-methylsulfonyl, 4-aminosulfonyl, hydrogen, 2-, 3-, or 4-halogen, $C_1$–$C_6$-alkyl, cyclopentyl, cyclohexyl, $C_1$–$C_4$-alkoxy, hydroxy, cyano, nitro, amino and trifluoromethyl;

$R_2$ is selected from the group consisting of 4-methylsulfonyl, 4-aminosulfonyl, hydrogen, 2-, 3-, or 4-halogen, C1–C6-alkyl, cyclopentyl, cyclohexyl, $C_1$–$C_4$-alkoxy, hydroxy, cyano, nitro, amino and trifluoromethyl; and $R_3$ is selected from the group consisting of hydrogen, methyl, ethyl, n-propyl, i-propyl, c-propyl, n-butyl, isobutyl; provided that when $R_1$ is a methylsulfonyl or aminosulfonyl group, $R_2$ is any group as defined above except a methylsulfonyl or aminosulfonyl group; and when $R_2$ is a methylsulfonyl or aminosulfonyl group, $R_1$ is any group as defined above except a methylsulfonyl or aminosulfonyl group;

with the further proviso that at least one of $R_1$ or $R_2$ is selected from either a methylsulfonyl group or an aminosulfonyl group;

said process comprising the steps of:

(A) reacting an aminosulfonyl or methylsulfonyl-substituted styrene oxide with a primary amine in a lower alkyl alcohol medium at the temperature ranging from about 0° C. to 60° C., to yield N-alkyl-beta-hydroxy-aminosulfonyl(or methylsulfonyl)phenethyl amine;

(B) acylating the resulting N-alkyl-beta-hydroxy-aminosulfonyl(or methylsulfonyl)phenethyl amine with a phenactyl chloride having substituent(s), selected from the group consisting of hydrogen, 2-, 3-, or 4-halogen, $C_1$–$C_6$-alkyl, cyclopentyl, cyclohexyl, $C_1$–$C_4$-alkoxy, hydroxy, cyano, nitro, amino or trifluorormethyl, at room temperature, to yield N-alkyl-N-[2-hydroxy-2-(aminosulfonyl(or methylsulfonyl)phenyl)ethyl-4substituted pheacetamide;

(C) oxidizing the N-alkyl-N-[2-hydroxy-2-(aminosulfonyl(or methylsulfonyl)phenyl)ethyl-4-substituted pheacetamide using Jone's reagent or pyridine-chromic anhydride solution to yield N-alkyl-N-[2-oxo-2-(aminosulfonyl(or methylsulfonyl)phenyl)ethyl-4-substituted pheacetamide;

(D) alcoholating the N-alkyl-N-[2-oxo-2-(aminosulfonyl (or methylsulfonyl)phenyl)ethyl-4-substituted pheacetamide under the catalysis of potassium or sodium lower alkyl alcoholate to yield the desired sulfonyl-containing 3,4-diaryl-3-pyrrolin-2-ones compound.

32. The process of claim 31, wherein the process further comprises the steps of:

(A) reacting primary amine with styrene oxide substituted by a component selected from the group of hydrogen, 2-, 3-, or 4-halogen, $C_1$–$C_6$-alkyl, cyclopentyl, cyclohexyl, $C_1$–$C_4$-alkoxy, hydroxy, cyano, nitro, amino or trifluoromethyl in a lower alkyl alcohol medium at the temperature from about 0° C. to 60° C., to yield N-alkyl-beta-hydroxy-substituted phenethylamine;

(B) further reacting the resulting N-alkyl-beta-hydroxy-substituted phenethylamine with aminosulfonyl(or mnethylsulfonyl) and a phenactyl chloride at room temperature under triethylamine or pyridine, to yield N-alkyl-N[2-hydroxy-2-substituted phenyl)ethyl-4-(aminosulfonyl(or methylsulfonyl)) pheacetamide;

(C) using Jone's reagent or pyridine-chromic anhydride solution to oxidize the N-alkyl-N-[2-hydroxy-2-(substituted phenyl)ethyl-4-(aminosulfonyl(or methylsulfonyl))pheacetamide to yield N-alkyl-N-[2-oxo-2-substituted phenyl)ethyl-4-(aminosulfonyl(or methylsulfonyl)) pheacetamide;

(D) under the catalysis of potassium or sodium lower alkyl alcoholate, cycling the N-alkyl-N-[2-oxo-2-(substituted phenyl) ethyl-4-(aminosulfonyl(or methylsulfonyl))pheacetamide to yield the desired sulfonyl-containing 3,4-diaryl-3-pyrrolin-2-ones compound.

33. The process of claim 31, wherein the lower alkyl alcoholate includes methanol, ethanol, 2-propanol, isopropanol or tert-buty alcohol.

34. The process of claim 32, wherein the lower alkyl alcoholate includes methanol, ethanol, 2-propanol, isopropanol or tert-buty alcohol.

35. A method for treating rheumatoid arthritis of mammalian animals, including humans, said method comprising the step of administering a therapeutically effective amount of a compound according to claim 1 to a subject.

* * * * *